US008293488B2

(12) United States Patent
Kelleher-Andersson et al.

(10) Patent No.: US 8,293,488 B2
(45) Date of Patent: Oct. 23, 2012

(54) METHOD FOR SCREENING NEUROGENIC AGENTS

(75) Inventors: Judith Kelleher-Andersson, Columbia, MD (US); Karl K. Johe, Potomac, MD (US)

(73) Assignee: Neuralstem, Inc., Rockville, MD (US)

( * ) Notice: Subject to any disclaimer, the term of this patent is extended or adjusted under 35 U.S.C. 154(b) by 1038 days.

(21) Appl. No.: 11/852,922

(22) Filed: Sep. 10, 2007

(65) Prior Publication Data

US 2008/0057530 A1    Mar. 6, 2008

Related U.S. Application Data

(62) Division of application No. 10/728,652, filed on Dec. 5, 2003, now abandoned.

(60) Provisional application No. 60/432,359, filed on Dec. 9, 2002.

(51) Int. Cl.
*G01N 33/567* (2006.01)
(52) U.S. Cl. .................. 435/7.21; 435/368; 435/377
(58) Field of Classification Search .................. None
See application file for complete search history.

(56) References Cited

U.S. PATENT DOCUMENTS

| | | |
|---|---|---|
| 4,753,635 A | 6/1988 | Sagen et al. |
| 4,980,174 A | 12/1990 | Sagen et al. |
| 5,082,670 A | 1/1992 | Gage |
| 5,166,065 A | 11/1992 | Williams et al. |
| 5,175,103 A | 12/1992 | Lee et al. |
| 5,411,883 A | 5/1995 | Boss et al. |
| 5,580,777 A | 12/1996 | Bernard et al. |
| 5,589,376 A | 12/1996 | Anderson et al. |
| 5,612,211 A | 3/1997 | Wilson et al. |
| 5,672,499 A | 9/1997 | Anderson et al. |
| 5,693,482 A | 12/1997 | Anderson et al. |
| 5,750,376 A | 5/1998 | Weiss et al. |
| 5,753,505 A | 5/1998 | Luskin |
| 5,753,506 A | 5/1998 | Johe |
| 5,770,414 A | 6/1998 | Gage et al. |
| 5,824,489 A | 10/1998 | Anderson et al. |
| 5,849,553 A | 12/1998 | Anderson et al. |
| 5,851,832 A | 12/1998 | Weiss et al. |
| 5,928,947 A | 7/1999 | Anderson et al. |
| 6,040,180 A | 3/2000 | Johe |
| 6,071,889 A | 6/2000 | Weiss et al. |
| 6,284,539 B1 | 9/2001 | Bowen et al. |
| 6,294,346 B1 * | 9/2001 | Weiss et al. .................. 435/7.21 |
| 6,497,872 B1 | 12/2002 | Weiss et al. |
| 6,531,464 B1 | 3/2003 | Szabo et al. |
| 6,696,039 B2 | 2/2004 | Kung et al. |
| 6,699,871 B2 | 3/2004 | Edmondson et al. |
| 7,101,709 B2 | 9/2006 | Weiss et al. |
| 7,250,294 B2 * | 7/2007 | Carpenter et al. ............ 435/377 |
| 2002/0107273 A1 | 8/2002 | Nakao et al. |

FOREIGN PATENT DOCUMENTS

| | | |
|---|---|---|
| EP | 0 233 838 | 8/1987 |
| WO | WO 89/03872 | 5/1989 |
| WO | WO 90/06757 | 6/1990 |
| WO | WO 91/02003 | 2/1991 |
| WO | WO 91/09936 | 7/1991 |
| WO | WO 91/17242 | 11/1991 |
| WO | WO 93/01275 | 1/1993 |
| WO | WO 93/09802 | 5/1993 |
| WO | WO 94/02593 | 2/1994 |
| WO | WO 94/03199 | 2/1994 |
| WO | WO 94/04675 | 3/1994 |
| WO | WO 94/10292 | 5/1994 |
| WO | WO 95/13364 | 5/1995 |
| WO | WO 96/09543 | 3/1996 |
| WO | WO 96/15226 | 5/1996 |
| WO | WO 98/48001 | 10/1998 |
| WO | WO 99/01159 | 1/1999 |
| WO | WO 99/11758 | 3/1999 |

OTHER PUBLICATIONS

Palmer T.D. et al. Progenitor cells from human brain after death, Nature, May 3, 2001, vol. 411, pp. 42-43.*
Kaji T. et al. Establishment and characterization of immortalized hippocampal neural precursor cell lines, Cytotechnology, 2000, vol. 33, pp. 53-61.*
Roy N.S. et al. In vitro neurogenesis by progenitor cells isolated from the adult human hippocampus, Nature Medicine, Mar. 2000, vol. 6, No. 3, pp. 271-277.*
Conover et al., Ciliary Neurotrophic Factor Maintains the Pluripotentiality of Embryonic Stem Cells, Development 119, pp. 559-565 (1993).
Escary et al., Leukaemia Inhibitory Factor is Necessary for Maintenance of Haematopoietic Stem Cells and Thymocyte Stimulation, Nature, vol. 363, pp. 361-364 (May 27, 1993).
Evrard et al., Immortalization of bipotential and plastic glio-neuronal precursor cells, Proc. Natl. Acad. Sci. USA vol. 98, pp. 3062-3066, Apr. 1990 Developmental Biology.
Guentert-Lauber, et al., Responsiveness of Astrocytes in Serum-Free Aggregate Cultures to Epidermal Growth Factor: Dependence on the Cell and the Epidermal Growth Factor Concentration, Dev. Neurosci. 7: pp. 286-295 (1985).
Hollenberg et al., Epidermal Growth Factor: Receptors in Human Fibroblasts and Modulation of Action by Cholera Toxin, Proc. Natl. Acad. Sci. USA vol. 70, No. 10, pp. 2964-2968 (1973).
Monnet-Tschudi et al., Influence of Epidermal Growth Factor on the Maturation of Fetal Rat Brain Cells in Aggregate Culture, Dev. Neurosci. 11: pp. 30-40 (1989).
Resnick et al., Long-term Proliferation of Mouse Primordial Germ Cells in Culture, Nature, vol. 359, pp. 550-551 (Oct. 8, 1992).
Rudland et al., Growth Control in Cultured Mouse Fibroblasts: Induction of the Pleiotypic and Mitogenic Responses by a Purified Growth Factor, Proc. Natl. Acad. Sci. USA vol. 71, No. 7, pp. 2600-2604 (1974).
Ryder et al., Establishment and characterization of Multipotent Neural Cell Lines Using Retrovirus Vector-Mediated Oncogene Transfer, Journal of Neurobiology, vol. 21, No. 2, pp. 356-375 (1989).

(Continued)

*Primary Examiner* — Jon P Weber
*Assistant Examiner* — Satyendra Singh
(74) *Attorney, Agent, or Firm* — Morrison & Foerster LLP

(57) ABSTRACT

A method for discovering neurogenic drugs is revealed. The method allows for systematic screening of test agents such as libraries of compounds. The method consists of exposing test agents to cultures of differentiating neural progenitor cells and measuring their effects on increasing the overall cell number and/or the number of neurons.

3 Claims, 8 Drawing Sheets

OTHER PUBLICATIONS

Almazan et al., "Epidermal Growth and Bovine Growth Hormone Stimulate Differentiation and Myelination of Brain Cell Aggregates in Culture," Developmental Brain Research, 21:257-264 (1985).

Almazan, G. et al, "Triiodothyronine Stimulation of Oligodendroglial Differentiation and Myelination," Dev. Neurosci, vol. 7, pp. 45-54, 1985.

Anchan, R.M et al, "EFG and TGF-α Stimulate Retinal Neuroepithelial Cell Proliferation In Vitro," Neuron, vol. 6, pp. 923-936, 1991.

Arsenijevic Y. et al, "Isolation of multipotent neural precursors residing in the cortex of the adult human brain," Experimental Neurology, vol. 170, pp. 48-62, 2001.

Avellana-Adalid, V. et al., "Expansion of Rat Oligodendrocyte Progenitors into Proliferative "Oligospheres" that Retain Differentiation Potential," Journal of Neuroscience Research, vol. 45, pp. 558-570, 1996, http://www3.interscience.wiley.com/cgi-bin/abstract/67559/ABSTRACT.

Baetge, E., "Neural Stem Cells for CNS Transplantation," Annals New York Academy of Sciences, vol. 695, pp. 285-291 (1993).

Barlett, P.F. et al., "Immortalization of mouse neural precursor cells by the c-*myc* oncogene," Neurobiology, vol. 85, pp. 3255-3259, 1998.

Barlett, P.F., "Regulation fo Neural Precursors Differentitation in the Embryonic and Adult Forebrain," Clinical and Experimental Pharmacology and Physiology, vol. 22, pp. 559-562(1995).

Behl C., "Apoptosis and Alzheimer's disease," Journal of Neural Transmission, vol. 107, pp. 1325-1344, 2000.

Bernard, O. et al., "Role of the c-*myc* and the N-*myc* Proto-Oncogenes in the Immortalization of Neural Precursors," Journal of Neuroscience Research, vol. 24, pp. 9-20, 1989.

Birren, S.J. et al., "A v-myc-Immortalized Sympathoadrenal Progenitor Cell Line in Which Neuronal Differentiation Is Initiated by FGF but Not NGF," Neuron, vol. 4, pp. 189-201, 1990.

Bredesen, D.E. et al., "Neural Transplantation Using Temperature-sensitive Immortalized Neural Cells: A Preliminary Report," Annals of Neurology, vol. 27, pp. 205-207, 1990.

Bremner, J. D. et al., "Hippocampal volume reduction in major depression," Am. J. Psychiatry, vol. 157, pp. 115-117, 2000.

Brezun, J. et al., "Depletion in serotonin decreases neurogenesis in the dentate gyrus and the subventricular zone of adult rats," Neuroscience, vol. 89, pp. 999-1002, 1999.

Broe, M. et al., "Relationship between DNA fragmentation, morphological changes and neuronal loss in Alzheimer's disease and dementia with Lewy bodies," Acta Neuropathol, vol. 101, pp. 616-624, 2001.

Brustle, O., "Embryonic Stem Cell-Derived Glial Precursors: A source of Myelinating Transplants," Science, vol. 285, pp. 754-756 (1999).

Calof A L. et al., "Analysis of neurogenesis in a mammalian neuroepithelium: proliferation and differentiation of an olfactory neuron precursor in vitro," Neuron, vol. 3, pp. 115-127, 1999.

Cambray-Deakin, M.A. The expression of excitatory amino acid binding sites during neuritogenesis in the developing rat cerebellum. Ref. No. 78577. Biol Abstr vol. 90, 1990.

Cameron H A. et al., "Regulation of neurogenesis by growth factors and neurotransmitters," Journal of Neurobiology, vol. 36, pp. 287-306, 1998.

Cao Q. et al., "Stem Cell Repair of Central Nervous System Injury," Journal of Neuroscience Research, vol. 68, pp. 501-510, 2002.

Carpenter, M.K. et al., "Generation and Transplantation of EGF-Responsive Neural Stem Cells Derived from GFAP-hNGF Transgenic Mice," Experimental Neurology, vol. 148, pp. 187-204 (1997).

Carpenter, M.K. et al., "In Vitro Expansion of a Multipotent Population of Human Neural Progenitor Cells," Experimental Neurology, vol. 158, p. 265-278 (1999).

Castillo S.O. et al., "Dopamine Biosynthesis is Selectively Abolished in Substantia Nigra/Ventral Tegmental Area but Not in Hypothalamic Neurons in Mice with Targeted Disruption of the Nurr1 Gene," Molecular and Cellular neuroscience, vol. 11, pp. 36-46 (1998).

Castillo S.O. et al., "Organization, Sequence, Chromosomal Localization, and Promoter Identification of the Mouse Orphan Nuclear Receptor Nurr1 Gene," Genomics, vol. 41, pp. 250-257 (1997).

Cattaneo, E. et al., "Proliferation and differentiation of neuronal stem cells regulated by nerve growth factor," Letters to Nature, vol. 347, pp. 762-765, 1990.

Cepko, C.L., "Immortalization of Neural Cells Via Retrovirus-Mediated Oncogene Transduction," Annu. Rev. Neurosci., vol. 12, pp. 47-65, 1989.

Chabot, P. Transient expression of an intermediate filament-associated protein (IFAPa-400) during in vivo and in vitro differentiation of chick embryonic cells derived form neuroectoderm. Ref. No. 78577. Biol Abstr vol. 90, 1990.

Coon H G. et al., "Cell cultures of neuroblasts from rat olfactory epithelium that show odorant responses," Neurobiology, vol. 86, pp. 1703-1707, 1989.

Coppell, A. L. et al., "Bi-phasic change in BDNF gene expression following antidepressant drug treatment," Neuropharmcaology, vol. 44, pp. 903-910, 2003.

Czeh, B. et al., "Stress-induced changes in cerebral metabolites, hippocampal volume, and cell proliferation are prevented by antidepressant treatment with tianepine," PNAS, vol. 98, pp. 12796-12801, 2001.

Davis, A.A. et al., "A self-renewing multipotential stem cell in embryonic rat cerebral cortex," Letters to Nature, vol. 375, pp. 263-266 (1994).

DiCicco-Bloom, E. et al., "Neuroblast Mitosis in Dissociated Culture: Regulation and Relationship to Differentiation," The Journal of Cell Biology, vol. 110, pp. 2073-2086, 1990.

Drago, J. et al., :Fibroblast Growth Factor-Mediated Prolifereation of Central Nervous System Precursors Depends on Endogenous Production of Insulin-like Growth Factor I, Neurobiology, vol. 88, pp. 2199-2203, 1991.

Drago, J. et al., "A Method for the Isolation of Purified Murine Neuroepithelial Cells From the Developing Mouse Brain," Journal of Neuroscience Methods, vol. 37, pp. 251-256, 1991.

Drago, J. et al., "Basic Fibroblast Growth Factor Upregulates Steady-State Levels of Laminin B1 and B2 Chain mRNA in Cultured Neuroepithelial Cells," Experimental Cell Research, vol. 196, pp. 246-254, 1991.

Drago, J. et al., "Laminin through its Long Arm E8 Fragment Promotes the Proliferation and Differentiation of Murine Neuroepithelial Cells in Vitro," Experimental Cell Research, vol. 192, pp. 256-265, 1991.

D'Sa, C. et al., "Antidepressants and neuroplasticity," Bipolar Disorders, vol. 4, pp. 183-194, 2002.

Dutton, G.R. "Isolation, Culture, and Use of Viable Central nervous System Perikarya," Methods in Neuroscience, vol. 2, pp. 87-102, 1990.

Ehrlich, M.E. et al. "DARPP-32 development in the caudate nucleus is independent of afferent input from the substantia nigra," Ref. No. 78577. Biol Abstr vol. 90, 1990.

Eilers, M. et al., "Chimaeras of Myc oncoprotein and steroid receptors cause hormone-dependent transformation of cells," Letters to Nature, vol. 340, pp. 66-68 (1989).

Eriksson P S. et al., "Neurogenesis in the adult human hippocampus," Nature Medicine, vol. 4, pp. 1313-1317, 1998.

Falk A. et al., "Amphiregulin is a mitogen for adult neural stem cells," Journal of Neuroscience Research vol. 69, pp. 757-762, 2002.

Feron F. et al., "Stress induces neurogenesis in non-neuronal cell cultures of adult olfactory epithelium" Neuroscience, vol. 88, pp. 571-583, 1999.

Finger S. et al., "Nimodipine and Neural Grafts," Duke Med Cent Lib 34.P2, p. 208, 1991.

Fischer, A.J. et al., "Exogenous Growth Factors Induce the Production of Ganglion Cells at the Retinal Margin," Development, vol. 129, pp. 2283-2291, 2002.

Flax, J.D. et al., "Engraftable human neural stem cells respond to developmental cues, replace neurons, and express foreign genes," Nature Biotechnology, vol. 16, pp. 1033-1039 (1998).

Frappaz, D. et al., "Enhancement of Growth of Primary Metastatic Fresh Human Tumors of the Nervous System by Epidermal Growth Factor in Serum-free Short Term Culture," Neurosurgery, vol. 23, pp. 355-359, 1998.

Frederiksen, K. et al., "Immortalization of Precursor Cells for the Mammalian CNS," Neuron, vol. 1, pp. 439-448, 1988.

Gage, F.H. et al., "Isolation, Characterization, and Use of Stem Cells From The CNS," Ann. Rev. Neurosci., vol. 18, pp. 159-192 (1995).

Glasky et al., "Update: Central and Peripheral Nervous Systems AIT-082, a novel purine derivative with neuroregenerative properties," Exp. Opin. Invest. Drugs, vol. 6, pp. 1413-1417, 1997.

Godfraind, C. et al., "In Vivo Analysis of Glial Cell Phenotypes During a Viral Demyelinating Disease in Mice," The Journal of Cell Biology, vol. 109, pp. 2405-2416, 1989.

Goldman S A. et al., "In vitro neurogenesis by neuronal precursor cells derived from the adult songbird brain," The Journal of Neuroscience, vol. 12, pp. 2532-2541, 1992.

Gould E. et al., "Inaugural Article: Adult-generated hippocampal and neocortical neurons in macaques have a transient existence," PNAS, vol. 98, pp. 10910-10917, 2001.

Green, S. et al., "Human oestrogen receptor cDNA: sequence, expression and homology to v-erb-A," Nature, vol. 320, pp. 134-139 (1986).

Gritti, A. et al., "Multipotential Stem Cells from the Adult Mouse Brain Proliferate and Self-Renew in Response to Basic Fibroblast Growth Factor," The Journal of Neuroscience, vol. 16, pp. 1091-1100 (1996).

Gu W. et al., "Cortical neurogenesis in adult rats after reversible photothrombotic stroke," Journal of Cerebral Blood Flow and Metabolism, vol. 20, pp. 1166-1173, 2000.

Hall et al, 1992, An Introduction to Molecular Neurobiology, p. 357.

Hata, M. et al., "A decrease in the wet-dog shakes response to the second administration of kainic acid in juvenile rats," Ref. No. 31832, Biol Abstr vol. 92, 1991.

Hauser K F. et al., "Opioids intrinsically inhibit the genesis of mouse cerebellar granule neuron precursors in vitro: differential impact of mu and delta receptor activation on proliferation and neurite elongation," European Journal of Neuroscience, vol. 12, pp. 1291-1293, 2000.

Hermanson, M. et al., "PDGF and its receptors following facial nerve axotomy in rats: expression in neurons and surrounding glia," Exp Brain Res., vol. 102, pp. 415-422 (1995).

Honegger, P. et al., "Growth and Differentiation of Aggregating Fetal Brain Cells in a Serum-Free Defined Medium," Nature, vol. 282, pp. 305-308, 1979.

Honkaniemi, J. et al., "Focal brain injury induces multiple immediate early genes encoding zinc finger transcription factors," Molecular Brain Research, vol. 28, pp. 157-163 (1995).

Horcholle-Bossavit, G. et al., "Postnatal development of peroneal motoneurons in the kitten," Ref. No. 78577. Biol Abstr vol. 90, 1990.

Hoshimaru, M. et al., "Differentiation of the immortalized adult neuronal progenitor ce line HC2S2 into neurons by regulatable suppression of the v-myc oncogene," Neurobiology, vol. 93, pp. 1518-1523 (1996).

Howland et al., "Focal loss of the glutamate transporter EAAT2 in a transgenic rat model of SOD1 mutant-mediated amyotrophic lateral sclerosis (ALS)," PNAS, vol. 99, pp. 1604-1609, 2002.

Hunter, S.F. et al., "Growth factor responses of enriched bipotential glial progenitors," Ref. No. 78577, Biol Abstr vol. 90, 1990.

Ishibashi et al., "Human Neural Stem/Progenitor Cells, Expanded in Long-Term Neurosphere Culture, Promote Functional Recovery After Focal Ischemia in Mongolian Gerbils," Journal of Neuroscience Research, vol. 78, pp. 215-223, 2004.

Jelitai M. et al., "Regulated appearance of NMDA Receptor Subunits and Channel Functions Duriing In Vitro Neuronal Differentiation," Journal of Neurobiology, vol. 51, pp. 54-65, 2002.

Jin K. et al., "Stem cell factor stimulates neurogenesis in vitro and in vivo." The Journal of Clinical Investigation, vol. 110, pp. 311-319, 2002.

Jin K. et al., "Vascular endothelial growth factor (VEGF) stimulates neurogenesis in vitro and in vivo," PNAS, vol. 99, pp. 11946-11950, 2002.

Jones-Villeneuve, et al., "Retinoic Acid Induces Embryonal Carcinoma Cells to Differentiate into Neurons and Glial Cells," The Journal of Cell Biology, vol. 94, pp. 253-262, 1982.

Jung, M. et al., "Novel pluripotential neural progenitor lines exhibiting rapid controlled differentiation to neurotransmitter receptor-expressing neurons and glia," European Journal of Neuroscience, vol. 10, pp. 3246-3256 (1998).

Kehl L J. et al., "Neurogenesis in postnatal rat spinal cord: a study in primary culture," Science, vol. 276, pp. 586-589, 1997.

Kempermann, G. et al., "Depressed new neurons-adult hippocampal neurogenesis and a cellular plasticity hypothesis of major depression," Biological Psychiatry, vol. 54, pp. 499-503, 2003.

Kempermann, G. et al., "Genetic determinants of adult hippocampal neurogenesis correlate with acquisition, but not probe trial performance, in the water maze task," European Journal of Neuroscience, vol. 16, pp. 129-136, 2002.

Kershaw, T.R. et al., "Foetal H-2K$^b$-tsA58 Transgenic Mouse Tissue Develops in a Similar Manner to ISO Geneic Foetal Tissue when Transplanted into Adult Mouse Brain," Duke Med Cent Lib 34.P4, p. 208, 1991.

Kilpatrick et al., "Cloning and Growth of Multipotential Neural Precursors: Requirements for Proliferation and Differentiation," vol. 10, pp. 255-265, 1993.

Kilpatrick, T.J. et al., "Cloned Multipotential Precursors from the Mouse Cerebrum Require FGF-2, Whereas Glial Restricted Precursors are Stimulated with Either FGF-2 or EGF," vol. 15, pp. 3653-3661 (1995).

Kilpatrick, T.J. et al., "The Regulation of Neural Precursor Cells within the Mammalian Brain," Molecular and Cellular Neuroscience, vol. 6, pp. 2-15 (1995).

Kitani, H. et al., "Isolation and Characterization of Mouse Neural Precursor Cells in Primary Culture," In Vitro Cell. Dev. Biol., vol. 27A, pp. 615-624, 1991.

Kuhn, H. G. et al., "Neurogenesis in the dentate gyrus of the adult rat: age-related decrease of neuronal progeneitor proliferation," The Journal of Neuroscience, vol. 16, pp. 2027-2033, 1996.

Kumar, V. et al., "Localisation of the oestradiol-binding and putative DNA-binding domains of the human oestrogen receptor," The EMBO Journal, vol. 5, pp. 2231-2235 (1986).

Law, S.W. et al., "Identification of a new Brain-Specific Transcription Factor, NURR1," Molecular Endocrinology, vol. 6, pp. 2129-2135 (1992).

Lee, A. L. et al., "Stress and depression: possible links to neurons death in the hippocampus," Bipolar Disorders, vol. 4, pp. 117-128, 2002.

Lee, C.M. et al., "The v-myc oncogene," Oncogene, vol. 18, pp. 2997-3003 (1999).

Lee, J. et al., "Dietary restriction increases the number of newly generated neural cells, and induces BDNF expression, in the dentate gyrus of rats," Journal of Molecular Neuroscience, vol. 15, pp. 99-108, 2001.

Lichtenwalner, R. J. et al., "Intracerebroventricular infusion of insulin-like growth factor-1 ameliorates the age-related decline in hippocampal neurogenesis," Neuroscience, vol. 107, pp. 603-613, 2001.

Ling, Z.D. et al., "Differentiation of Mesencephalic Progenitor Cells into Dopaminergic Neurons by Cytokines," Experimental Neurology, vol. 149, pp. 411-423 (1998).

Lois, C. et al., "Proliferating subventricular zone cells in the adult mammalian forebrain can differentiate into neurons and glia," Proc. Natl. Acad. Sci, vol. 90, pp. 2074-2077 (1993).

Lovejoy, D.A. et al., "Primary structure of two forms of gonadotropin-releasing hormone from brains of the American alligator," Ref. No. 31832, Biol Abstr vol. 92, 1991.

Lucassen, P. J. et al., "Hippocampal apoptosis in major depression is a minor event and absent from subareas at risk for glucocorticoid overexposure," American Journal of Pathology, vol. 158, pp. 453-468, 2001.

Lyman, W.D. et al., " Human Fetal Central Nervous System Organotypic Cultures," Developmental Brain Research, vol. 60, pp. 155-160, 1991.

Ma W. et al., "Acetylcholine stimulates cortical precursor cell proliferation in vitro via muscarinic receptor activation and MAP kinase phosphorylation," European Journal of Neuroscience, vol. 12, pp. 1227-1240, 2000.

Madsen T M. et al., "Increased neurogenesis in a model of electroconvulsive therapy," Biological Psychiatry, vol. 47, pp. 1043-1049, 2000.

Mages, H.W. et al., "NOT, A human Immediate-Early Response Gene Closely Related to the Steroid/Thyroid Hormone Receptor NAK1/TR3," Molecular Endocrinology, vol. 8, pp. 1583-1591 (1994).

Malberg, J. E. et al., "Chronic antidepressant treatment increases neurogenesis in adult rat hippocampus," The Journal of Neuroscience, vol. 20, pp. 9104-9110, 2000.

Marin N. et al., β.-amyloid-induced activation of caspase-3 in primary cultures of rat neurons, Mechanisms of Ageing and Development, vol. 119, pp. 63-67, 2000.

Masters, B.A. "Insulin-like growth factor I (IFG-I) receptors and IGF-I action in oligodendrocytes from rat brains." Ref. No. 31832, Biol Abstr vol. 92, 1991.

Mauerhoff, T. et al., Differential Expression and Regulation of Major Histocompatibility Complex (MHC) Products in Neural and Glial Cells of the Human Fetal Brain, Journal of Neuroimmunology, vol. 18, pp. 271-289, 1988.

Mayo W. et al., "Pregnenolone sulfate and aging of cognitive functions: behavioral, neurochemical, and morphological investigations," Hormones and Behavior, vol. 40, pp. 215-217, 2001.

McCarthy, M. et al., "Infection of Human Neural Cell Aggregate Cultures with a Clinical Isolate of Cytomegalovirus," Journal of Neuropathology and Experimental Neurology, vol. 50, pp. 441-450, 1991.

McKay, R. et al., "Mechanisms Regulating Cell number and Type in the Mammalian Central Nervous System," Cold Spring Harbor Symposia on Quantitative Biology, vol. LV, pp. 291-301, 1990.

Mervaala, E. et al., "Quantitative MRI of the hippocampus and amygdala in severe depression," Psychological Medicine, vol. 30, pp. 117-125, 2000.

Morrison, R.S. et al., "Trophic Stimulation of Cultured Neurons from Neonatal Rat Brain by Epidermal Growth Factor," Science, vol. 238, pp. 72-75, 1987.

Murphy, M. et al., "Fibroblast Growth Factor Stimulates the Proliferation and Differentiation of Neural Precursor Cells In Vitro," Journal of Neuroscience Research, vol. 25, pp. 463-475, 1990.

Murrell W. et al., "Neurogenesis in adult human," Neuroreport, vol. 7, pp. 1189-1194, 1996.

Mytilineou, C. et al., "Epidermal Growth Factor-Induced Survival and Proliferation of Neuronal Precursor Cells from Embryonic Rat Mesencephalon," Neuroscience Letters, vol. 135, pp. 62-66, 1992.

Nakafuku et al., "Establishment and Characterization of a Multipotential Neural Cell Line That Can Conditionally Generate Neurons, Astrocytes, and Oligodendrocytes In Vitro," Journal of Neuroscience Research, vol. 41, pp. 153-168, 1995.

Nakagawa, S. et al., "Regulation of neurogenesis in adult mouse hippocampus by cAMP and the cAMP reponse element-binding protein," The Journal of Neuroscience, vol. 22, pp. 3673-3682, 2002.

Nestler, E. J. et al., "Neurobiology of Depression," Neuron, vol. 34, pp. 13-25, 2002.

Nibuya M. et al., "Chronic antidepressant administration increases the expression of cAMP response element binding protein (CREB) in rat hippocampus." The Journal of Neuroscience, vol. 16, pp. 2365-2372, 1996.

Nielsen, F.C. et al., "Receptor Binding, Endocytosis, and Mitogenesis of Insulin-Like Growth Factors I and II in Fetal Rat Brain Neurons," Journal of Neurochemistry, vol. 56, pp. 12-21, 1991.

Ohkura, N. et al., "Structure, mapping and expression of a human NOR-I gene, the third member of the Nur77/NGFI-B family," Biobhimica et Biophysica Acta, vol. 1308, pp. 205-214 (1996).

Okabe, T. et al., "cDNA Cloning of a NGFI-B/nur77-Related Transcription Factor from an Apoptotic Human T Cell Line," The Journal of Immunology, vol. 154, pp. 3871-3879 (1995).

Okano et al., "Neural stem cells and regeneration of injured spinal cord," Kidney International, vol. 68, pp. 1927-1931, 2005.

Okano, H., "Neural stem cells: progression of basic research and perspective for clinical application," Keio Journal of Medicine, vol. 51, pp. 115-128, 2002.

Palmer T D. et al., "Fibroblast growth factor-2 activates a latent neurogenic program in neural stem cells from diverse regions of the adult CNS," The Journal of Neuroscience, vol. 19, pp. 8487-8497, 1999.

Park K. et al., "Global gene and cell replacement strategies via stem cells," Gene Therapy, vol. 9, pp. 613-624, 2002.

Peña de Ortiz, S. et al., "HZF-3, an immediate-early orphan receptor homologous to NURR1/NOT: Induction upon membrane depolarization and seizures," Molecular Brain Research, vol. 38, pp. 1-13 (1996).

Perrone-Capano, C. et al., "Epigenetic factors and midbrain dopaminergic neurone development," BioEssays, vol. 18, pp. 817-824 (1996).

Peterson D. A. et al., "Trophic factor therapy for neuronal death," Alzheimer Disease, $2^{nd}$ Edition, Chapter 25, pp. 373-388, 1999.

Pham, K. et al., "Repeated restraint stress suppresses neurogenesis and induces biphasic PSA-NCAM expression in the adult dentate gyrus," European Journal of Neuroscience, vol. 17, pp. 879-886, 2003.

Piescinski, P. et al., "Neurogenesis of the amygdaloid complex in the rhesus monkey," Society for Neuroscience Abstracts, vol. 16, p. 1147, 1990.

Pincus D W. et al., "In vitro neurogenesis by adult human epileptic temporal neocortex," Clinical Neurosurgery, Chapter 2, pp. 17-25, 1997.

Pollerberg et al., "Generation of Cell Lines From Embryonic Quail Retina Capable of Mature Neuronal Differentiation," Journal of Neuroscience Research, vol. 41, pp. 427-442, 1995.

Pucilowski, O. et al., Decreased hyperthermic effect of MK801 in selectively bred hypercholinergic rats, Ref. No. 31832, Biol Abstr vol. 92, 1991.

Puliam, L. et al., "A Normal Human Brain Cell Aggregate Model for Neurobiological Studies," Journal of Neuroscience Research, vol. 21, pp. 521-230, 1988.

Qu, T. et al., "Human neural stem cells improve cognitive function of aged brain," NeuroReport, vol. 12, pp. 1127-1132, 2001.

Raina, A K. et al., "Abortive apoptosis in Alzheimer's disease," Acta Neuropathol, vol. 101, pp. 305-310, 2001.

Rao, M.S. et al., "Immortalization and Controlled In Vitro Differentiation of Murine Multipotent Neural Crest Stem Cells," J. Neurobiol., vol. 32, pp. 722-746 (1997).

Rathbone M P. et al., "Trophic effects of purines in neurons and glial cells," Progress in Neurobiology, vol. 59, pp. 663-690, 1999.

Ray, J. et al., "Proliferation, differentiation, and long-term culture of primary hippocampal neurons," Neurobilogy, vol. 90, pp. 3602-3606 (1995).

Ray, J. et al., "Spinal Cord Neuroblasts Proliferate in Response to Basic Fibroblast Growth Factor," The Journal of Neuroscience, vol. 14, pp. 3548-3564 (1994).

Reichmann, E. et al., "Activation of an Inducible c-FosER Fusion Protein Causes Loss of Epithelial Polarity and Triggers Epithelial-Fibroblastoid Cell Conversion," Cell, vol. 71, pp. 1103-1116 (1992).

Renoncourt, Y. et al., "Neurons derived in vitro from ES cells express homeoproteins characteristic of motoneurons and interneurons," Mechanisms of Development, vol. 79, pp. 185-197 (1998).

Rettig, W.J. et al., "Cell Type-specific Control of Human Neuronectin Secretion by Polypeptide mediators and Phorbol Ester," The Journal of Histochemistry and Cytochemistry, vol. 37, pp. 1777-1786, 1989.

Rettig, W.J. et al., "Stimulation of Human Neuronectin Secretion by Brain-Derived Growth Factors," Brain Research, vol. 487, pp. 171-177, 1989.

Reynolds, B.A. et al., "A Multipotent EFG-Responsive Striatal Embryonic Progenitor Cell Produces Neuron and Astrocytes," The Journal of Neuroscience, vol. 12, pp. 4565-4574, 1992.

Reynolds, B.A. et al., "A Non-Transformed, Growth Factor Dependent Stem Cell Line Derived From the Embryonic Mouse CNS Produces Neurons, Astrocytes and Oligodendrocytes," Duke Med Cent Lib 34.P3, p. 208, 1991.

Reynolds, B.A. et al., "EGF- and TFGα-responsive striatal embryonic progenitor cells produce both neurons and astocytes," Society for Neuroscience Abstracts, vol. 16, p. 1147, 1990.

Reynolds, B.A. et al., "Generation of Neurons and Astocytes from Isolated Cells of the Adult Mammalian Central Nervous System," Science, vol. 255, pp. 1707-1709, 1992.

Riber, E.F. et al., "Establishment and Characterization of Multipotent Neural Cell Lines Using Retrovirus Vector-Mediated Oncogene Transfer," Journal of Neurobiology, vol. 21, pp. 356-375 (1990).

Righi, M. et al., "myc-Immortalized Microglial Cells Express a Functional Platelet-Activating Factor Receptor," Journal of Neurochemistry, vol. 64, pp. 121-129 (1995).

Rind H. et al., "Synaptic Targeting of Retrogradely Transported Trophic Factors in Mononeurons: Comparison of Glial Cell Line-Derived Neurotrophic Factor, Brain-Derived Neurotrophic Factor, and Cardiotrophin-1 with Tetanus Toxin," The Journal of Neuroscience, vol. 25, pp. 539-549, 2005.

Romand, R. et al., "Development of tonotopy oin the inferior colliculus: 1. Electrophysiological mapping in house mice," Ref. No. 78577. Biol Abstr vol. 90, 1990.

Roth, K. A., "Caspases, apoptosis, and Alzheimer disease: causation, correlation, and confusion," Journal of Neuropathology and Experimental Neurology, vol. 60, pp. 829-838, 2001.

Rothstein J.D. et al., "Decreased Glutamate Transport by the Brain and Spinal Cord in Amyotrophic Lateral Sclerosis," The New England Journal of Medicine, vol. 326, pp. 1464-1468, 1992.

Roy N S, et al., "In vitro neurogenesis by progenitor cells isolated from the adult human hippocampus," Nature Medicine, vol. 6, pp. 271-277, 2000.

Rozental R. et al., "Differentiation of hippocampal progenitor cells in vitro: temporal expression of intercellular coupling and voltage- and ligand-gated responses," Developmental Biology, vol. 167, pp. 350-362, 1995.

Rutka, J.T. et al., "Characterization of Fetal Human Brain Cultures," Dev. Neurosci., vol. 9, pp. 154-173, 1987.

Sabate, O. et al., "Transplantation to the rat brain of human neural progenitors that were genetically modified using adenoviruses," Nature Genetics, vol. 9, pp. 256-260 (1995).

Sah, W.Y. et al., "Bipotent progenitor cell lines from the human CNS," Nature biotechnology, vol. 15, p. 574-580 (1997).

Sales, N. et al., Neutral endopeptidase 24.11 in rat peripheral tissues: comparative localization bby "ex vivo" and "in vitroautoradiography," Ref. No. 31832, Biol Abstr vol. 92, 1991.

Saneto, R.P. et al., "Insulin/Insulin-Like Growth Factor I and Other Epigenetic Modulators of Myelin Basic Protein Expression in Isolated Oligodendrocyte Progenitor Cells," Journal of Neuroscience Research, Vo. 21, pp. 210-219, 1988.

Santarelli, L. et al., "Requirement of hippocampal neurogenesis for the behavioral effects of antidepressants," Science, vol. 301, pp. 805-809, 2003.

Sapolsky, R. M., "The possibility of neurotoxicity in the hippocampus in major depression: a primer on neuron death.," Biological Psychiatry, vol. 48, pp. 755-765, 2000.

Sato, H. et al., "Somatostatin receptors in the senescent rat brain: A quantitative autoradiographic study," Ref. No. 31832, Biol Abstr vol. 92, 1991.

Satoh M. et al., "Promotion of neurogenesis in mouse olfactory neuronal progenitor cells by leukemia inhibitory factor in vitro," Neuroscience Letters, vol. 225, pp. 165-168, 1997.

Saucedo-Cardenas, O. et al., "Cloning and structural organization of the gene encoding the murine nuclear receptor transcription factor, NURR1," Gene, vol. 87, pp. 135-139 (1997).

Saucedo-Cardenas, O. et al., "Nurr1 is essential for the induction of the dopaminergic phenotype and the survival of ventral mesencephalic late dopaminergic precursor neurons," Proc. Natl. Acad. Sci. USA 95:4013-4018 (1998).

Scearce et al., "RNR-1, a Nuclear Receptor in the NGFI-B/Nur77 Family That is Rapidly Induced in Regenerating Liver," J. Biol. Chem. 268:8855-8861 (1993).

Schapira, B., "Pathogenesis of Parkinson's disease," Clin. Neurol. 6:15-36 (1997).

Scott B W. et al., "Neurogenesis in the dentate gyrus of the rat following electroconvulsive shock seizures," Experimental Neurology, vol. 165, pp. 231-236, 2000.

Seaberg R M. et al., "Adult rodent neurogenic regions: the ventricular subependyma contains neural stem cells, but the dentate gyrus contains restricted progenitors," The Journal of Neuroscience, vol. 22, pp. 1784-1793, 2002.

Seigel, G.M. et al., "Differentiation of oncogenically altered chick neuroretinal cells by succinylated concanavalin A," Society for Neuroscience Abstracts, vol. 16, p. 1147, 1990.

Selvakurmaran, M. et al., "Myeloblastic Leukemia Cells Conditionally Blocked by Myc-Estrogen Receptor Chimeric Transgenes for Terminal Differentiation Coupled to Growth Arrest and Apoptosis," Blood, vol. 81, pp. 2257-2262 (1993).

Sheline, Y. I. et al., "Hippocampal atrophy in recurrent major depression," Proc. Natl. Acad. Sci. USA, vol. 93, pp. 3908-3913, 1996.

Shingo T. et al., "Erythropoietin regulates the in vitro and in vivo production of neuronal progenitors by mammalian forebrain neural stem cells," The Journal of Neuroscience, vol. 21, pp. 9733-9743, 2001.

Shirayama, Y. et al., "Brain-derived neurotrophic factor produces antidepressant effects in behavioral models of depression," The Journal of Neuroscience, vol. 22, pp. 3251-3261, 2002.

Shors T J. et al., "Neurogenesis in the adult is involved in the formation of trace memories," Nature, vol. 410, pp. 372-376, 2001.

Shou J. et al., "BMPs inhibit neurogenesis by a mechanism involving degradation of a transcription factor," Nature Neuroscience, vol. 2, pp. 339-345, 1999.

Silani, V. et al., "Human Neuronal Cells in Culture: From Concepts to Basic Methodology," Boll. 1st. Sieroter. Mila., vol. 69, pp. 309-313, 1990.

Sorensen, K.A. et al., "Postembryonic neurogenesis in the Brain of *Manduca Sexta*," Society for Neuroscience Abstracts, vol. 16, p. 1147, 1990.

Stemple, D.L. et al., "Neural Stem Cells Are Blasting Off," Neuron, vol. 18, pp. 1-4 (1997).

Sternfeld, M.D. et al., "Cultured Human Retinal Pigment Epithelial Cells Express Basic Fibroblast Growth Factor and its Receptor," Current Eye Research, vol. 8, pp. 1029-1037, 1989.

Stewart, J.S. et al., "Olfactory bulb and sensory epithelium in goldfish: Morphological alterations accompanying growth," Ref. No. 78577. Biol Abstr vol. 90, 1990.

Stone et al., "Definition of Regions in Human c-myc That Are Involved in Transformation and Nuclear Localization," Molecular and Cellular Biology 7: 1697-1709, 1987.

Svendsen, "Neurones from stem cells," Trends in Neuroscience 18, 465-466 (1995).

Svendsen, C.N. et al., "Increased survival of rat EGF-generated CNS precursor cells using B27 supplemented medium," Exp. Brain Res. 102, 407-44114 (1995).

Takahashi J. et al., "Retinoic acid and neurotrophins collaborate to regulate neurogenesis in adult-derived neural stem cell cultures," J Neurobiol, vol. 38, pp. 65-81, 1999.

Takahashi, T. et al., "Cell cycle kinetics of the E14 murine cerebral ventricular zone: estimates based upon S-Phase labeling with BUdR," Society for Neuroscience Abstracts, vol. 16, p. 1147, 1990.

Taupin P, et al., "FGF-2-responsive neural stem cell proliferation requires CCg, a novel autocrine/paracrine cofactor," Neuron, vol. 28, pp. 385-397, 2000.

Taylor, M. et al., "Induction of Differentiation of Rat Retinal, Germinal, Neuroepithelial Cells by dbcAMP," Journal of Neurobiology, vol. 21, pp. 470-481, 1990.

Temple, S., "Division and Differentiation of Isolated CNS Blast Cells in Microculture," Nature, vol. 340, pp. 471-473-1989.

Tenot, M. et al., Epidermal Growth Factor Enhances the Expression of an Edogenous Lectin in Aggregating Fetal Brain Cell Cultures, Journal of Neurochemistry, vol. 53, pp. 1435-1441, 1989.

Torelli, S. et al., "Human Fetal Brain Cultures: A Model to Study Neural Proliferation, Differentiation and Immunocompetence," Adv. Exp. Med. Biol, vol. 296, pp. 121-134, 1991.

Tones, R.A. et al., "Alteration of Neuronal Regulation of Astrocytoma Proliferation by Insertional Mutagenesis," Society for Neuroscience Abstracts, vol. 16, p. 1147, 1990.

Turner M.R. et al., "Abnormal cortical excitability in sporadic but not homozygous D90A SOD1 ALS," J Neurol Neurosurg Psychiatry, vol. 76, pp. 1279-1285, 2005.

Unsicker et al., "Growth factor function in the development and maintenance of midbrain dopaminergic neurons: concepts, facts and prospects for TGF-β," Ciba Found. Symp. 196:70-84 (1996).

Van Praag et al., " Running enhances neurogenesis, learning, and long-term potentiation in mice," PNAS, vol. 96, pp. 13427-13431, 1999.

Van Praag et al., "Running increases cell proliferation and neurogenesis in the adult mouse dentate gyrus," Nature Neuroscience, vol. 2, pp. 266-270, 1999.

Vescovi et al., "Isolation and Cloning of Multipotential Stem Cells from the Embryonic Human CNS and Establishment of Transplantable Human Neural Stem Cell Lines by Epigenetic Stimulation," Experimental Neurology, vol. 156, pp. 71-83 (1999).

Vescovi, A.L. et al., "bFGF Regulated the Proliferative Fate of Unipotent (Neuronal) and Bipotent (Neuronal/Astroglial) EGF-Generated CNS Progenitor Cells," Neuron 11, 951-966 (1993).

Vicario-Abejon, C. et al., "Functions of Basic Fibroblast Growth Factor and Neurotrophins in the Differentiation of Hippocampal Neurons," Neuron 15, 105-114 (1995).

Villa, A. et al., "Intracellular calcium ion stores in chicken purkinje neurons; Differential distribution of the low affinity-high capacity calcium binding protein, calsequestrin, of calcium ATPase and of the ER luminal protein," Bip. Ref. No. 31832, Biol Abstr vol. 92, 1991.

Von Frijtag, J. C. et al., "Chronic imipramine treatment partially reverses the lnog-term changes of hipocampal synaptic plasticity in socially stressed rats," Neuroscience Letters, vol. 309, pp. 153-156, 2001.

Von Visger, J.R. et al., "Differentiation and Maturation of Astrocytes Derived from neuroepithelial Progenitor Cells in Culture," Experimental Neurology 128: 34-40, 1994.

Vu, E.T. et al., "Evidence for a Computational Distinction Between Proximal and Distal Neuronal Inhibition," Science, vol. 255, pp. 1710-1712, 1992.

Wagner et al, "Induction of midbrain dopaminergic phenotype in Nurr1-overexpressing neural stem cells by type 1 astrocytes," Nat. Biotech., 17: 653-659 (1999).

Wainer, B.H. et al., "In vitro cell cultures as model of the basal forebrain," Adv Exp Med Biol., vol. 295, pp. 415-437, 1991.

Wang et al. "A regulatory system for use in gene transfer," (1994) PNAS 91,8180.

Wang et al., "Induction of dopaminergic neurono phenotype in the midbrain by Sonic hedgehog protein," Nature Medicine, vol. 1, pp. 1184-1188, 1995.

Watanabe, R.T. et al., "Rod Photoreceptor development in vitro: intrinsic properties of proliferating neuroepithelial cells change as development proceeds in the rat retina," NeuralCulture, Abstract, 1990.

Watt et al., "Nucleotide sequence of cloned cDNA of human c-myc oncogene," Nature 303: 725-728, 1983.

Weiss et al., "Multipotent CNS Stem Cells are Present in the Adult Mammalian Spinal Cord and Ventricular Neuroaxis," The Journal of Neuroscience, vol. 16, pp. 7599-7609, 1996.

Wohl C A, et al., "Retinoic acid enhances neuronal proliferation and astroglial differentiation in cultures of CNS stem cell-derived precursors," J Neurobiol, vol. 37, pp. 281-290, 1998.

Wolswijk et al., "Identification of an adult-specific glial progenitor cell" Development, 105:387-400 (1989).

Xing et al., "Rat nurr1 is prominently expressed in perirhinal cortex, and differentially induced in the hippocampal dentate gyrus by electroconvulsive vs. kindled seizures," Molecular Brain Research, vol. 47, pp. 251-261, 1997.

Xu et al., "The extremem C terminus of progesterone receptor contains a transcriptional repressor domain that functions through a putative corepressor," Proc. Natl. Acad. Sci., vol. 93, pp. 12195-12199, 1996.

Xu, L. et al., "Glucocorticoid receptor and protein/RNA synthesis-dependent mechanisms underlie the control of synaptic plasticity by stress," PNAS, vol. 95, pp. 3204-3208, 1998.

Yamada et al., "NMDA receptor mediated $Ca^{2+}$ responses in neurons differentiated from $p53^{-/-}$ immortalized Murine neural stem cells," (1999) Neurosci. Letters 264,165.

Yan J. et al., "Differentiation and Tropic/Trophic Effects of Exogenous Neural Precursors in the Adult Spinal Cord," vol. 480, pp. 101-114, 2004.

Yan, J. et al., "Grafted Human Neural Stem (NS) Cells Differentiate Into Neurons, Migrate Long Distance and Project Axons in Spinal Cord and the Roots of Adult Rats," Program No. 150.19, Abstract Viewer/Ininerary Planner. Society for Neuroscience, 2003.

Ye et al., "FGF and Shh Signals Control Dopaminergic and Serotonergic Cell Fate in the Anterior Neural Plate," Cell 93:755-766 (1998).

Yoshimoto, Y. et al, "The Effect of Cool Storage on the Survivability of Intraventricular Rat Fetal Ventral Mesencephalic Graft," Duke Med Cent Lib 34.P1, p. 208, 1991.

Zetterstrom et al., "Cellular expression of the immediate early transcription faxtors Nurr 1 and NGFI-B suggests a gene regulatory role in several brain regions including the nigrostriatal dopamine system," Molecular Brain Research, vol. 41, pp. 111-120, 1996.

Zetterstrom et al., "Dopamine Neuron Agenesis in Nurr1-Deficient Mice," Science 276:248-250 (1997).

Zhang, R. et al, "A nitric oxide donor induces neurogenesis and reduces functional deficits after stroke in rats," Ann. Neurol., vol. 50, pp. 602-611, 2001.

Weiss et al., Reexamination Control No. 90/008366 for Patent No. 7,101,709, Methods of Screening Biological Agents, request for reexamination dated Dec. 7, 2006.

Weiss et al., Reexamination Control No. 90/008366 for Patent No. 7,101,709, Methods of Screening Biological Agents; Office Action in Ex Parte Reexamination, dated Sep. 8, 2007.

Weiss et al., Reexamination Control No. 90/008367 for Patent No. 6,294,346, Use of Multipotent Neural Stem Cells and Their Progeny for the Screening of Drugs and Other Biological Agents, request for reexamination dated Dec. 7, 2006.

Weiss et al., Reexamination Control No. 90/008367 for Patent No. 6,294,346, Use of Multipotent Neural Stem Cells and Their Progeny for the Screening of Drugs and Other Biological Agents; Office Action in Ex Parte Reexamination, dated Jul. 18, 2008.

Weiss et al., Reexamination Control No. 90/008580 for Patent No. 5,851,832, In Vitro Growth and Proliferation of Multipotent Neural Stem Cells and Their Progeny, request for reexamination dated Apr. 5, 2007.

Weiss et al., Reexamination Control No. 90/008580 for Patent No. 5,851,832, In Vitro Growth and Proliferation of Multipotent Neural Stem Cells and Their Progeny; Office Action dated Sep. 7, 2007.

Weiss et al., Reexamination Control No. 90/008581 for Patent No. 6,497,872, Neural Transplantation Using Proliferated Multipotent Neural Stem Cells and Their Progeny, request for reexamination filed Apr. 5, 2007.

Weiss et al., Reexamination Control No. 90/008581 for Patent No. 6,497,872, Neural Transplantation Using Proliferated Multipotent Neural Stem Cells and Their Progeny; Office Action in Ex Parte Reexamination dated Sep. 8, 2007.

Carpenter, Reexamination Control No. 90/008862 for Patent No. 6,103,530, Cultures of Human CNS Neural Stem Cells, request for reexamination dated Oct. 2, 2007.

* cited by examiner

METHOD FOR SCREENING NEUROGENIC AGENTS

CROSS REFERENCE TO RELATED APPLICATIONS

The present application is a divisional of U.S. patent application Ser. No. 10/728,652, filed Dec. 5, 2003 which claims priority to and the benefit of U.S. Provisional Application No. 60/432,359, filed Dec. 9, 2002, each of which are incorporated herein in their entirety by reference

BACKGROUND

According to a long-held doctrine, no significant number of neurons are made and contribute to function in the adult mammalian nervous system. However, recent data indicate that adult mammalian brains contain neural precursor cells capable of generating new neurons both in normal and in injured conditions. These new neurons have been quantified in live animals by injecting or feeding in drinking water a marker of dividing cells, bromodeoxyuridine (BrdU) and by immunostaining of post-mortem brains with antibodies against BrdU and neuronal markers. An endogenous marker of dividing cells, ki67 protein, has also been used instead of BrdU for this purpose. Thus, in healthy, young rodents, approximately 3,000-15,000 new cells per day are estimated to be born in the dentate gyrus of the hippocampus, about 60% of which express early neuron-specific proteins such as doublecortin and type III beta-tubulin. Significant number of new cells and new neurons have also been observed in healthy, young primates. In rodents as well as in primates, the location of neurogenic areas in the CNS is limited to the dentate gyrus of the hippocampus and the subependymal layer of the striatum. In human patients of different ages who have been diagnosed with a tumor of the tongue, a single injection of BrdU has revealed significant number of new cells and new neurons being born in the dentate gyrus and the subependymal layer of the striatum. Thus, the process of generating new neurons (neurogenesis) occurs in the mature, adult brain in significant quantities throughout rodents, primates, and human species.

Such significant quantities of new neurons suggest that they may be important for the normal physiology of the brain, especially the hippocampus. Hippocampus is the well-known center of learning, memory, and other cognitive functions, processes which new information are added, edited, stored, and recalled constantly throughout life. Since hippocampus is also the most potent neurogenic area of the brain, many studies have been undertaken to establish whether neurogenesis may be the cellular mechanism to structurally accommodate the ever-increasing volume of cognitive processing to be handled. Thus, it has been shown that at least some of the newly born neurons, marked by genetic markers, do mature to be electrophysiologically active and integrate into the existing neuronal circuitry of the hippocampus. Ablation of the neurogenesis in rats leads to decreased cognitive capabilities in several behavior tests. Thus, the existing data demonstrate that neurogenesis significantly contributes to the normal hippocampal physiology.

In abnormal conditions, such as when an injury to a brain area has occurred, neurogenesis becomes more wide-spread and perhaps functionally diverse. In rodent models of ischemic and hemorrhagic stroke, the newly born neurons of the subependyma (also referred to as subventricular zone) are seen migrating to and accumulating in the lesion area of the cortex. However, the newly born neurons have short survival period.

Thus, a compound that can stimulate the endogenous neurogenesis either in a disease state or in a healthy state may be an effective drug for a number of human nervous system diseases. However, the current limitation is the lack of an effective, predictive in vitro assay that can be used to select a neurogenic compound for clinical drug development. Disclosed here is a novel, in vitro assay, which is effective and predictive, to be useful for discovering a compound that promotes neurogenesis in vivo. Also disclosed are classes of compound structures that are shown to be particularly effective in promoting the neurogenesis.

This invention relates to the method of discovering a neurogenic drug to treat neurologic, psychiatric, and aging-related disorders. It also relates to the use of Fused Imidazoles, Aminopyrimidines, Nicotinamides, Aminomethyl Phenoxypiperidines and Aryloxypiperidines for use as therapeutic agents and analytical reagents by means of promoting neurogenesis. More particularly this invention relates to these agents as therapeutics for prevention and treatment of neurological diseases in mammals and reagents for detecting neurogenesis and proliferation.

Most antidepressants are thought to work by increasing the levels of monoamines available for post-synaptic receptors. Examples of classes of agents working apparently by the "monoaminergic hypothesis of depression" include the selective serotonin uptake inhibitors (SSRIs) like fluoxetine, the mixed noradrenaline/serotonin transporter blockers like tricyclic agent imipramine and noradrenaline uptake inhibitors like desipramine. The antidepressant-induced increase in intraneuronal biogenic amines occurs quite rapidly. However, the antidepressant-induced improvement in clinical behavior requires weeks of daily administration.

One hypothesis that may account for the slow-onset of the antidepressants' therapeutic activity is that they work by promoting hippocampal neurogenesis. It is expected that neurogenesis would require a number of weeks for stem cells to divide, differentiate, migrate and establish connections with post-synaptic neurons. The neurogenesis theory of depression then postulates that antidepressant effect is brought about by structural changes in the hippocampal circuitry contributed by newly generated neurons stimulated by antidepressants (Malberg et al., 2000; Czeh et al, 2001; Santarelli et al, 2003).

The neurogenic theory of depression, though not conclusive, has strong supportive data including the finding that neurogenesis is actually requisite for antidepressant behavioral improvement in the novelty suppressed feeding model (Santarelli et al., 2003). A therapeutic benefit from hippocampal neurogenesis is further supported by the finding of hippocampal atrophy in depression, where MRI imaging studies identified a reduction in the right and the left hippocampal volumes in individuals with major depression (Sheline et al., 1996; Bremner et al., 2000; Mervaala et al., 2000). Long standing works also suggest a strong relationship between glucocorticoid dysregulation or glucocorticoid hypersecretion in stress and depression, such that the hippocampal volume loss might be considered a consequence of glucocorticoid-induced hippocampal neuronal loss (Sheline et al., 1996; Lucassen et al., 2001; Lee et al., 2002 (review)). Furthermore, in studies which involved the administration of a chronic stress to animals, both hippocampal volume changes and reduction in neurogenesis were observed, and these events were both reversed by chronic antidepressant administration (Czeh et al., 2001; Pham et al., 2003), further illustrating the strong association between depression, stress and neurogenesis. The association comes full circle, since agents or conditions that promote a reduction in neurogenesis also appear as causative agents/events in depression, specifically glucocorticoid (Sapolsky, 2000), and depletion of serotonin (Brezun and Da_szuta, 1999). Kempermann and Kronenberg (2003), though acknowledging the validity of the hippocampal neurogenesis theory of depression, suggest that this hypothesis needs to be looked at in the context of a larger model of cellular plasticity, which elucidates how antidepressants induce nascent neurons of unknown phenotype to survive and produce viable circuits.

Neurogenesis can be characterized as three successive stages: proliferation of endogenous stem cells and precursors, differentiation into neurons and neuron maturation with formation of viable synaptic connections (plasticity). By taking into account all stages of neurogenesis, then the hippocampal volume loss in depression could potentially be caused by 1) inhibition of the endogenous hippocampal stem cell proliferation in the dentate gyrus, 2) inhibition of differentiation and dendrite development and 3) by loss of neurons (apoptosis) and their dendritic structure. Though apoptosis is observed in depression, hippocampal apoptosis as measured by DNA fragmentation from depressed patients appears to play only a minor role in the volume loss (Lucassen et al., 2001). In an animal model of acute stress or in normal animals receiving exogenous corticosterone the stress did cause a reduction in synaptic plasticity in the hippocampus (Xu et al., 1998). Chronic administration of the tricyclic antidepressant, imipramine partially reversed the loss in LTP in socially stressed, depressive-like animals (Von Frijtag et al., 2001) suggesting imipramine effects on the plasticity phase of neurogenesis. In another animal model of depression, presenting neurogenesis loss and hippocampal volume loss, stressed animals that chronically received the antidepressant, tianeptine, showed similar numbers of dividing cells as control animals (no social stress) a measure of proliferation (Czeh et al., 2001). In an experiment looking at association of antidepressants and neurogenesis in normal adult rats, the antidepressant, fluoxetine required chronic administration to cause proliferation of cells in dentate gyrus (24 hrs post treatment), but there was considerable loss of nascent cells whether in the presence or absence of fluoxetine treatment, where fluoxetine provided no observed differentiation or survival benefit (Malberg et al.,2000). Results on different neurogenic intervention points by known antidepressants suggest that nova neurogenic agents that intervene at different points in the neurogenesis pathway, could result in potentially diverse therapeutic effects on depression.

These points of intervention can be studied and the target elucidated for novel antidepressant candidates through in vitro assays. Since adult stem cell proliferation and neurogenesis is observed in adult vertebrates in hippocampal dentate gyrus (Gould et al., 2001; Eriksson et al., 1998), we can use multi-potential hippocampal stem cells to screen agents in vitro for neurogenic activity.

Interestingly, chronic administration of either the antidepressant fluoxetine, an SSRI or the antidepressant rolipram, a phosphodiesterase IV inhibitor, promoted neurogenesis in normal animals (Malberg et al., 2000; Nakagawa et al., 2002). One might conclude from these results that any agent that promotes neurogenesis will generate a behavioral benefit in depression, unrelated to the agents mechanism-of-action or possibly there is a common pathway where both drug actions overlap. D'Sa and Duman (2002) suggest a scheme whereby the phosphorylation and activation of CREB and the subsequent expression of BDNF are central to the induction of neurogenesis, that culminates in antidepressant behavior. CREB phosphorylation is increased in animals administered rolipram chronically (Nakagawa et al., 2002) and antidepressants that either increase $Ca^2+$/CaM-kinases or cAMP could cause the phosphorylation of CREB in the nucleus (reviewed by D'sa and Duman 2002). They further suggest that the phosphorylated CREB then binds to CRE binding site to promote the expression of BDNF and bcl-2, that appear critical to cell survival and plasticity. Proof of neurotrophic factor BDNF's involvement in depression comes from studies showing that antidepressants and electroconvulsive shock both caused an increase in BDNF levels (Nibuya et al., 1996) and that intrahippocampal injection of BDNF had antidepressant activity in two models of depression (Shirayama et al., 2002).

If neurogenesis is critical for antidepressant activity is it also sufficient and is the mechanism by which the neurogenesis occurs or timing of neurogenesis also critical to the therapeutic activity? We can try to answer these questions using novel agents developed through screening paradigms that identify agents that promote the proliferation and differentiation of endogenous hippocampal stem cells to neurons in vivo if they will be effective antidepressants. Since we have completed the screening of 10,000 small molecule compounds in in vitro models of neurogenesis and shown that our in vitro screen is predictive of in vivo neurogenic efficacy, we can then test these orally available agents, that promote in vivo neurogenesis, in models of depression. Rolipram, an antidepressant that works by increasing cAMP levels and is neurogenic in animals (Nakagawa et al., 2002) was effective in our primary in vitro neurogenesis screen. This suggests that our primary in vitro screen would include those agents that might promote neurogenesis by targeting the cAMP/pCREB/BDNF pathway. This does not necessarily exclude all other neurogenesis mechanisms for our NSI compounds. If the target of these neurogenic agents are important for behavioral activity where three separate chemically diverse classes showed in vitro assay efficacy differences and that the mechanism for all does not overlap at the point of CREB phosphorylation and BDNF expression then we might expect very different effects on behavioral activities in depression models.

Neuropathology associated with key cognitive regions of the Alzheimer's diseased brain have led to therapeutic strategies that address the neuronal loss, in the hopes of reducing the cognitive decline. One strategy enlists trophic agents, that regulate neuronal function and survival, as AD therapeutics (see Peterson and Gage, 1999). Problems with systemic administration, side effects and locating trophic-sensitive neurons generated few clinical successes with these therapies. One AD therapeutic, AIT-082, promotes memory enhancement in AD individuals potentially by stimulating endogenous trophic factors (Ritzman and Glasky, 1999; Rathbone et al., 1999). So the use of agents to promote increased survival and function of the remaining available neurons appears to have some therapeutic value.

Hippocampus is one of the main brain regions where neurogenesis in adult brain has been documented across several vertebrate species, including monkeys and humans (e.g., Gould et al., 2001; Eriksson et al., 1998). In fact, adult hippocampal neurogenesis contributes functionally to cognitive capacity. Shors et al. (2001) reported that inhibition of neurogenesis in adult rat hippocampus, in the absence of the destruction of existing neurons, caused impaired memory function. Many studies observed that degenerative conditions induced neurogenesis in mature mammalian brains, suggesting the existence of a natural repair pathway by means of neurogenesis. A focal ischemic model, reversible photo-thrombic ring stroke, caused increased neurogenesis in rat cortex by 3-6% (Gu et al., 2000). Seizures induced by electroconvulsive shock in adult rats increased neurogenesis in dentate gyrus of hippocampus (Scott et al, 2000; Madsen et al, 2000). Also, rats gamma-irradiated to kill mitotic cells in the CNS showed reduced numbers of nascent neurons and reduced LTP in slice cultures. These observations highlight the likelihood that a cellular mechanism for neurogenesis within adult human CNS, especially in hippocampus, does exist both as a normal physiological process and as a self-repairing pathway.

In adult neurogenesis a decline due to aging is observed (Kuhn et al., 1996), though proof that this age-dependent decline in neurogenesis causes cognitive impairment is still debated. Considerable evidence does exist, indicating that increased neurogenesis reduces age-associated cognitive decline. This is most dramatically observed with the transplantation of human stem cells into aged rats initiating improved water maze learning and retention (Qu et al., 2001). Other data suggests that induction of neurogenesis by diet restriction (Lee et al., 2000) exercise (van Praag et al., 1999) or growth factor addition (Lichtenwalner et al, 2001) improves learning and memory in adult or aged rats. A number of other inducers of neurogenesis have been identified, including anti-depressants (Malberg et al., 2000; Czeh et al, 2001), and nitric oxide donors (Zhang et al., 2001) suggesting the usefulness of neurogenic agents for other diseases presenting cognitive-deficits, such as stroke and depression. A small molecule that induces hippocampal neurogenesis that is blood brain barrier penetrable would allow for a potentially novel oral therapeutic for Alzheimer's disease.

Other potential AD therapeutics progressing in clinical trials, target neurodegeneration in the hopes of reducing the neuronal loss and cognitive decline. Apoptotic death involving caspase pathways and DNA fragmentation has been measured in in vitro and animal models of AD and in Alzheimer's diseased brain tissue. The extent of apoptosis leading to neuronal loss is of continual debate with most agreeing it has some effect, but that other neuronal death pathways definitely play a role (see Behl, 2000; Broe et al., 2001; Roth, 2001). Concern that measures of upstream caspase markers in neurons from AD tissue may not proceed to degeneration has been suggested (Raina et al, 2001). In order to screen for a neuroprotectant therapeutics it is critical, therefore, to measure more than one endpoint of neuronal death and determine at what point an agent may intervene in the death pathway(s). Behl (2000) suggested that AD pathology is most likely a mixture of apoptotic and necrotic pathways and that concentrating therapeutic discovery using only one pathway may provide inconclusive results. All hits in our neurogenesis models were tested through our secondary apoptosis/necrosis assay to screen for agents that function both as neurogenic and neuroprotective agents. These agents may improve or reverse the cognitive decline observed in MCI and AD.

RELATED ART

Arsenijevic Y, Villemure J G, Brunet J F, Bloch J J, Deglon N, Kostic C, Zum A, Aebischer P. (2001). *Isolation of multipotent neural precursors residing in the cortex of the adult human brain*. Exp Neurol. vol 170(1):48-62.

Behl C. *Apoptosis and Alzheimer's disease*. (2000) J Neural Transm. Vol. 107 (11):1325-44.

Bremner, J. D., Narayan, M., Anderson, E. R., Staib, L. H., Miller, H. L. Chamey, D. S. (2000). *Hippocampal volume reduction in major depression*. Am. J. Psychiatry vol 157(1): 115-118.

Brezun, J M and Daszuta, A. (1999). *Depletion in serotonin decreases neurogenesis in the dentate gyrus and the subventricular zone of adult rats*. Neuroscience vol 89(4):999-1002.

Broe, M, Shepherd, C E, Milward, E A, and Halliday, G M. (2001) *Relationship between DNA fragmentation, morphological changes and neuronal loss in Alzheimer's disease and dementia with Lewy bodies*. Acta Neuropathol. (Berl) Vol. 101(6):616-624.

Calof A L, Chikaraishi D M. (1989). *Analysis of neurogenesis in a mammalian neuroepithelium: proliferation and differentiation of an olfactory neuron precursor in vitro*. Neuron. 3(1):115-27.

Cameron H A, Hazel T G, McKay R D. (1998). *Regulation of neurogenesis by growth factors and neurotransmitters*. J Neurobiol. vol 36(2):287-306.

Coon H G, Curcio F, Sakaguchi K, Brandi M L, Swerdlow R D. (1989). *Cell cultures of neuroblasts from rat olfactory epithelium that show odorant responses*. Proc Natl Acad Sci USA. vol 86(5):1703-7.

Coppell, A. L., Pei, Q., Zetterstrom, T. S. (2003) *Biphasic change in BDNF gene expression following antidepressant drug treatment*. Neuropharmacology vol 44(7):903-910.

Czeh, B., Michaelis, T., Watanabe, T., Frahm, J., de Biurrun, G., van Kampen, M., Bartolomucci, A., and Fuchs E. (2001). *Stress-induced changes in cerebral metabolites, hippocampal volume, and cell proliferation are prevented by antidepressant treatment with tianepine*. PNAS Vol. 98 (22): 12796-12801.

D'Sa, C., and Duman, D. C. (2002). *Antidepressants and neuroplasticity*. Bipolar Disorders vol 4:183-194.

Eriksson P S, Perfilieva E, Bjork-Eriksson T, Alborn A M, Nordborg C, Peterson D A, Gage F H. (1998). *Neurogenesis in the adult human hippocampus*. Nat Med. vol 4 (11):1313-7.

Falk A, Frisen J. (2002). *Amphiregulin is a mitogen for adult neural stem cells*. J Neurosci Res. vol 69(6):757-62.

Feron F, Mackay-Sim A, Andrieu J L, Matthaei K I, Holley A, Sicard G. (1999) *Stress induces neurogenesis in non-neuronal cell cultures of adult olfactory epithelium*. Neuroscience. vol 88(2):571-83.

Goldman S A, Zaremba A, Niedzwiecki D.(1992). *In vitro neurogenesis by neuronal precursor cells derived from the adult songbird brain*. J Neurosci. 12(7):2532-41.

Gould E, Vail N, Wagers M, Gross C G. (2001) *Inaugural Article: Adult-generated hippocampal and neocortical neurons in macaques have a transient existence*. Proc. Natl. Acad. Sci. USA. vol 98(19):10910-10917.

Gu W, Brannstrom T, Wester P. (2000) *Cortical neurogenesis in adult rats after reversible photothrombotic stroke*. J Cereb Blood Flow Metab Vol. 20(8):1166-1173.

Hauser K F, Houdi A A, Turbek C S, Elde R P, Maxson W 3rd. (2000). *Opioids intrinsically inhibit the genesis of mouse cerebellar granule neuron precursors in vitro: differential impact of mu and delta receptor activation on proliferation and neurite elongation*. Eur J Neurosci. vol 12(4):1281-93.

Jelitai M, Schlett K, Varju P, Eisel U, Madarasz E. (2002) *Regulated appearance of NMDA receptor subunits and channel functions during in vitro neuronal differentiation*. J Neurobiol. vol 51(1):54-65.

Jin K, Mao X O, Sun Y, Xie L, Greenberg D A. (2002). *Stem cell factor stimulates neurogenesis in vitro and in vivo*. J Clin Invest. vol 110(3):311-9.

Jin K, Zhu Y, Sun Y, Mao X O, Xie L, Greenberg D A. (2002). *Vascular endothelial growth factor (VEGF) stimulates neurogenesis in vitro and in vivo*. Proc Natl Acad Sci USA. vol 99(18):11946-50.

Kehl L J, Fairbanks C A, Laughlin T M, Wilcox G L. (1997). *Neurogenesis in postnatal rat spinal cord: a study in primary culture*. Science. vol 276(5312):586-9.

Kempermann, G. and Kronenberg, G. (2003) *Depressed new neurons-adult hippocampal neurogenesis and a cellular plasticity hypothesis of major depression*. Biol Psychiatry vol 54 (5):499-503.

Kempermann, G. and Gage, F H (2002). *Genetic determinants of adult hippocampal neurogenesis correlate with acquisition, but not probe trial performance, in the water maze task*. Eur J of Neurosci, 16, 129-36.

Kuhn, H. G., Dickenson-Anson, H. and Gage, F. H. (1996) *Neurogenesis in the dentate gyrus of the adult rat: age-related decrease of neuronal progeneitor proliferation*. J. Neurosci. vol 16 (6), pp 2027-33.

Lee, A. L., Ogle, W. O., Sapolsky, R. M. (2002). *Stress and depression possible links to neurons death in the hippocampus*. Bipolar Disord. vol 4(2):117-128.

Lee, J., Duan, W., Long, J. M., Ingram, D. K., and Mattson, M. P. (2000) *Dietary restriction increases the number of newly generated neural cells, and induces BDNF expression, in the dentate gyrus of rats*. J. Mal. Neurosci. vol. 15 (2), pp 99-108.

Lichtenwalner, R. J., Forbes, M. E., Bennett, S. A., Lynch, C. D., Sonntag, W. E., and Riddle, D. R. (2001) *Intracerebroventricular infusion of insulin-like growth factor-1 ameliorates the age-related decline in hippocampal neurogenesis*. Neuroscience vol. 107 (4), pp 603-613.

Lucassen, P. J., Muller, M. B., Holsboer, F., Bauer, J., Holtrop, A., Wouda, J., Hoogendijk, W. J., DeKloet, E. R., Swaab, D. F. (2001). *Hippocampal apoptosis in major depression is a minor event and absent from subareas at risk for glucocorticoid overexposure*. Am. J. Pathol. vol 158(2): 453-468.

Ma W, Maric D, Li B S, Hu Q, Andreadis J D, Grant G M, Liu Q Y, Shaffer K M, Chang Y H, Zhang L, Pancrazio J J, Pant H C, Stenger D A, Barker J L. (2000). *Acetylcholine stimulates cortical precursor cell proliferation in vitro via muscarinic receptor activation and MAP kinase phosphorylation*. Eur J Neurosci. vol 12(4):1227-40.

Madsen T M, Treschow A, Bengzon J, Bolwig T G, Lindvall 0, Tingstrom A. (2000) *Increased neurogenesis in a model of electroconvulsive therapy*. Biol Psychiatry Vol. 47(12): 1043-1049.

Malberg, J. E., Eisch, A. J., Nestler, E. J., and Duman, R. S. (2000). *Chronic antidepressant treatment increases neurogenesis in adult rat hippocampus*. J. Neurosci. vol. 20 (24): 9104-9110.

Marin N, Romero B., Bosch-Morell F., Llansola M., Felipo V., Roma J., and Romero F. J. (2000) *β-amyloid-induced activation of caspase-3 in primary cultures of rat neurons*. Mech. Ageing and Devi. Vol. 119:63-67.

Mayo W, LeMoal M, Abrous D N. (2001) *Pregnenolone sulfate and aging of cognitive functions: behavioral, neurochemical, and morphological investigations*. Horm Behav Vol. vol 40(2):215-217.

Mervaala, E., Fohr, J., Kononen, M., Valkonen-Korhonen, M., Vainio, P., Partanen, K., Partanen, J., Tiihonen, J., Viinamaki, H., Karjalainen, A. K., Lehtonen, J. (2000). *Quantitative MRI of the hippocampus and amygdala in severe depression*. Psychol. Med. vol 30(1):117-125.

Murrell W, Bushell G R, Livesey J, McGrath J, MacDonald K P, Bates P R, Mackay-Sim A. (1996). *Neurogenesis in adult human*. Neuroreport vol 26;7(6): 1189-94.

Nakagawa, S., Kim, J-E, Le R., Malberg, J. E., Chen, J., Steffen, C., Zhang, Y-J., Nestler, E. J., Duman, R. S. (2002). *regulation of neurogenesis in adult mouse hippocampus by cAMP and the cAMP reponse element-binding protein*. J. Neurosci. vol 22(9):3673-3682.

Nibuya, M., Nestker, E, J., Duman, R. S. (1996). *Chronic antidepressant administration increases the expression of cAMP response element binding protein (CREB) in rat hippocampus*. Neurosci. Lett. vol 267:81-84.

Nestler, E. J., Barrot, M., DiLeone, R. J., Eisch, A., Gold, S. J., and Monteggia, L. M. (2002). *Neurobiology of Depression*. Neuron, vol 34:13-25.

Palmer T D, Markakis E A, Willhoite A R, Safar F, Gage F H. (1999) *Fibroblast growth factor-2 activates a latent neurogenic program in neural stem cells from diverse regions of the adult CNS*. J Neurosci. vol 19 (19):8487-97.

Peterson D. A. and Gage F. H. (1999) *Trophic factor therapy for neuronal death*. In: Alzheimer Disease, Terry, Katzman, Bick, Sisodia eds 2nd edition.

Pham, K., Nacher, J., Hof, P R., McEwen, B. S. (2003). *Repeated re-straint stress suppresses neurogenesis and induces biphasic PSA-NCAM expression in the adult dentate gyrus*. Eur. J. Neurosci. vol 17(2):879-886.

Pincus D W, Harrison-Restelli C, Barry J, Goodman R R, Fraser R A, Nedergaard M, Goldman S A. (1997). *In vitro neurogenesis by adult human epileptic temporal neocortex*. Clin Neurosurg. vol 44:17-25.

Qu, T, Brannan, C. L., Kim, H. M., and Sugaya, K. (2001) *Human neural stem cells improve cognitive function of aged brain*. Neuroreport vol. 12 (6), pp. 1127-32.

Raina, A K, Hochman A., Zhu, X., Rottkamp, C. A., Nunomura, A., Siedlak, S. L., Boux, H., Castellani, R. J., Perry, G., Smith, M. A. (2001) *Abortive apoptosis in Alzheimer's disease*. Acta Neuropahtol (Berl) Vol. 101(4):305-310.

Rathbone M P, Middlemiss P J, Gysbers J W, Andrew C, Herman M A, Reed J K, Ciccarelli R, Di Iorio P, and Caciagli F. (1999) *Trophic effects of purines in neurons and glial cells*. Prog. Neurobiol. Vol. 59(6):663-90.

Ritzman R, Glasky A J. (1997) *Psychopharmacological actions of AIT-082*. Soc. Neurosci. Abs. Vol. 23:1896.

Rozental R, Mehler M F, Morales M, Andrade-Rozental A F, Kessler J A, Spray D C. (1995). *Differentiation of hippocampal progenitor cells in vitro: temporal expression of intercellular coupling and voltage- and ligand-gated responses*. Dev Biol. 167(1):350-6.2.

Roth, K. A. (2001) *Caspases, apoptosis, and Alzheimer disease: causation, correlation, and confusion*. J. Neuropathol. Exp. Neurol. Vol. 60(9):829-838.

Roy N S, Wang S, Jiang L, Kang J, Benraiss A, Harrison-Restelli C, Fraser R A, Couldwell W T, Kawaguchi A, Okano H, Nedergaard M, Goldman S A. (2000) *In vitro neurogenesis by progenitor cells isolated from the adult human hippocampus*. Nat Med. vol 6(3):271-7.

Santarelli, L., Saxe, M., Gross, C., Surget, A., Battaglia, F., Dulawa, S., Weisstaub, N., Lee, J., Duman, R., Arancio, O., Belzung, C., and Hen, R. (2003). *Requirement of hippocampal neurogenesis for the behavioral effects of antidepressants*. Science vol 301:805-809.

Sapolsky, R. M. (2000). *The possibility of neurotoxicity in the hippocampus in major depression: a primer on neuron death*. Biol. Psychiatry vol 48(8):775-765.

Satoh M, Yoshida T. (1997). *Promotion of neurogenesis in mouse olfactory neuronal progenitor cells by leukemia inhibitory factor in vitro*. Neurosci Lett. vol 225(3):165-8.

Scott B W, Wojtowicz J M, Burnham W M. (2000) *Neurogenesis in the dentate gyrus of the rat following electroconvulsive shock seizures*. Exp Neurol Vol. 165(2):231-236.

Seaberg R M, van der Kooy. (2002) *Adult rodent neurogenic regions: the ventricular subependyma contains neural stem cells, but the dentate gyrus contains restricted progenitors*. J Neurosci. vol 22(5): 1784-93.

Sheline, Y. I., Wang, P. W., Gado, M. H., Csemansky, J. G., Vannier, M. W. (1996). *Hippocampal atrophy in recurrent major depression*. Proc. Natl. Acad. Sci. USA vol 93:3908-3913.

Shingo T, Sorokan S T, Shimazaki T, Weiss S. (2001). *Erythropoietin regulates the in vitro and in vivo production of neuronal progenitors by mammalian forebrain neural stem cells*. J Neurosci. vol 21(24):9733-43.

Shirayama, Y., Chen, A. C.-H., Nakagawa, S., Russell, D. S., Duman, R. S. (2002). *Brain-derived neurotrophic factor produces antidepressant effects in behavioral models of depression*. J. Neurosci. vol 22(8):3251-3261.

Shors T J, Miesegaes G, Beylin A, Zhao M, Rydel T, Gould E. (2001) *Neurogenesis in the adult is involved in the formation of trace memories*. Nature vol 410(6826):372-376.

Shou J, Rim P C, Calof A L. (1999). *BMPs inhibit neurogenesis by a mechanism involving degradation of a transcription factor*. Nat Neurosci. 2(4):301-3.

Takahashi J, Palmer T D, Gage F H. (1999). *Retinoic acid and neurotrophins collaborate to regulate neurogenesis in adult-derived neural stem cell cultures*. J Neurobiol. vol 38(1):65-81.

Taupin P, Ray J, Fischer W H, Suhr S T, Hakansson K, Grubb A, Gage F H. (2000). *FGF-2-responsive neural stem cell proliferation requires CCg, a novel autocrine/paracrine cofactor*. Neuron. vol 28(2):385-97.

Von Frijtag, J. C., Kamal, A., Reijmers, L. G., Schrama, L. H., van den Bos, R., Spruijt, B. M. (2001). *Chronic imipramine treatment partially reverses the long-term changes of hipocampal synaptic plasticity in socially stressed rats*. Neurosci. Lett. vol 309(3):153-156.

Wohl C A, Weiss S. (1998). *Retinoic acid enhances neuronal proliferation and astroglial differentiation in cultures of CNS stem cell-derived precursors*. J Neurobiol. vol 5;37(2): 281-90.

Xu, L., Holscher, C., Anwyl, R., Rowan, M. J. (1998). *Glucocorticoid receptor and protein/RNA synthesis-dependent mechanisms underlie the control of synaptic plasticity by stress*. PNAS USA. vol 95:3204-3208.

Zhang, R., Zhang, L., Zhang, Z., Wang, Y., Lu, M., Lapointe, M., and Chopp, M. (2001) *A nitric oxide donor induces neurogenesis and reduces functional deficits after stroke in rats*. Ann. Neurol. vol. 50 (5), pp 602-11.

SUMMARY

A neurogenic drug is an agent that enhances the process of generating new neurons (neurogenesis). Recent studies indicate that neurogenesis occurs in the adult human brains under normal as well as under degenerative conditions and that such adult-generated neurons do contribute functionally to the brain physiology such as learning and memory. These observations highlight the likelihood that a cellular mechanism for neurogenesis within adult human CNS, especially in hippocampus, does exist both as a normal physiological pathway and as a self-repairing pathway. What is lacking and contributes to permanent damage may be (1) the volume/persistence of neurogenesis and/or (2) the survival/maturation of the new neurons. The objective of the neurogenesis screen as described here is to discover a compound that will significantly boost either of these processes.

Many neurological diseases, including Alzheimer's disease, mild cognitive impairment, dementia, age-related cognitive decline, stroke, traumatic brain injury, spinal cord injury and the like are neurodegenerative conditions. Neuropsychiatric diseases including depression, anxiety, schizophrenia and the like also show nerve cell dysfunction leading to cognitive, behavioral, and mood disorders. A neurogenic drug would be beneficial for countering and treating these diseases.

The present invention discloses a method of discovering such a neurogenic drug. Such drug will serve to prevent or treat neurodegenerative and neuropsychiatric disorders by promoting the birth of new neuron endogenously within the nervous system by administering the compounds of the present invention into the patient. This may involve delivery of the agents alone or together with transplanted stem cells or progenitor cells.

Using the method herein, compounds of the type, Fused Imidazoles, Aminopyrimidines, Nicotinamides, Aminomethyl Phenoxypiperidines and Aryloxypiperidines are evaluated for their ability to promote neurogenesis by proliferation/differentiation of human hippocampal multipotent stem/progenitor cells and neuronal progenitors.

Additional features and advantages are described herein, and will be apparent from, the following Detailed Description and the figures.

DETAILED DESCRIPTION

Figure 1:
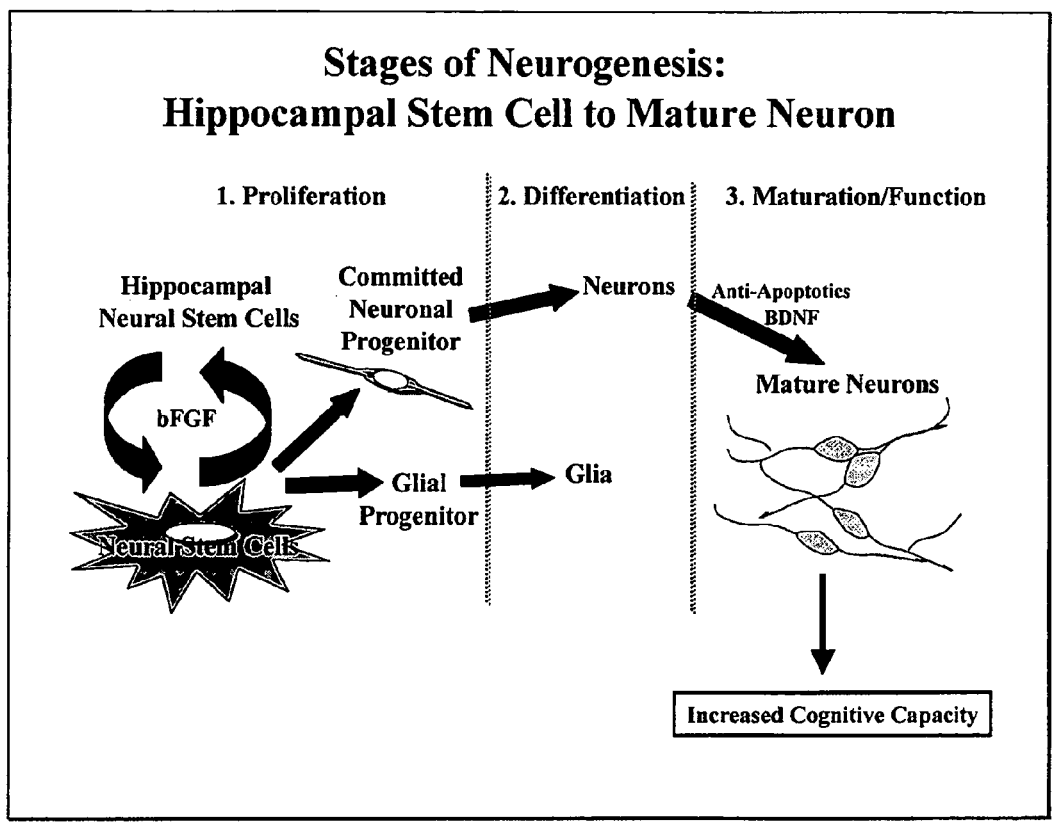
FIG. 1. Schematic description of neurogenesis processes captured in the assay and different potential sites of a neurogenic drug action.

1. A Stable Cell Line of Neural Progenitors

A screening of a large number of unknown agents (e.g., protein factors, peptides, nucleic acids, natural compounds, or synthetic compounds) for discovering a candidate drug involves repeating the same test for several hundreds to several million times. This requires a great deal of reproducibility from the test. In order to obtain such reproducibility for neurogenesis assay, we have created stable cell lines of neural progenitors, which upon differentiation generate reproducible quantities of neurons. In a preferred embodiment, a multipotent neural stem/progenitor cell line derived from human hippocampus was used. Cell lines derived from other CNS areas, including dentate gyrus of an adult brain, can also substitute. A neural progenitor population derived as a stable cell line from partial differentiation of embryonic stem cells can also be used. For this purpose, a cell line is defined as a population of cells having been expanded for at least 10 cell-doublings.

Cell lines that are genetically engineered to enhance the cells' mitotic capacity can also be used. In a preferred embodiment, the genetic modification consists of over-expression of functional c-myc protein intracellularly under a conditional activation system such as c-myc protein fused to a ligand-binding domain of an estrogen receptor. Cell lines that are not genetically engineered are preferred and can also be used.

In a preferred embodiment, a progenitor population that upon differentiation generates both neurons and glia in a single culture has been used. Presence of glia, either astrocytes and/or oligodendrocytes or their precursors, are required to promote physiological maturation of nascent neurons born from their precursors in culture.

In a preferred embodiment, differentiation of the progenitors is initiated by withdrawing the mitogen from the culture. Serum as well as other growth-promoting factors should be avoided from the differentiating culture since they will significantly affect the reproducibility and interfere with the neurogenesis assay.

2. Preparation of Assay Plate

Neural stem/progenitor cells differentiate spontaneously in the absence of a mitogen.

Undifferentiated mitotic cells are harvested by enzyme treatment to remove residual mitogen, in the preferred embodiment, basic fibroblast growth factor (bFGF). The collected cells are seeded into appropriate plates (standard 96-well or 384-well) pre-coated with the usual extra cellular matrix proteins (poly-D-lysine and fibronectin, for example) for attachment of the cells. The initial seeding density can be within the range of about 2,000-125,000 cells per well of a 96-well plate. The preferred density is 40,000 cells per well of a 96-well plate, which has been optimized for best signal-to-noise ratio. Too low cell density retards the initiation of differentiation and results in poor plating efficiency, which interferes with the assay. Too high cell density leads to inhibition of neurogenesis due to cell-cell contact and paracrine factors, which also interferes with the assay. The actual cell number can be proportionally decreased or increased depending upon the surface area of the culture substrate used. For example, for a 384-well plate, which has approximately ¼ of the surface area of a 96-well plate, the initial seeding density should be decreased accordingly (¼).

3. Detection of Neurogenesis

The key activity of a neurogenic drug is to increase the number of neurons generated from their precursors. A molecule can bring about such increase in the neurogenesis by a number of different mechanisms. It can act as a mitogen for the neural stem/progenitor cells and increase the progenitor's cell number, which in turn results in increased number of neurons in the culture when differentiated. Or, it can act as a neuronal specification factor by promoting the stem/progenitor cell differentiation toward neurons in the expense of glia. This will also result in increased number of neurons in the culture, but without changing the overall cell number. Or, it can act as a mitogen for committed neuronal progenitors that differentiate only into neurons. Increasing this subpopulation would also increase the final number of neurons in the culture. Or, it can act as a survival factor to rescue immature neurons from undergoing cell death during differentiation, which will result in increased neurons (FIG. 1).

The assay method here captures all of these possibilities by allowing for sufficient time for these processes to unfold. In a preferred embodiment, for human neural stem/progenitor cells, the assay is continued for seven days. A minimum of three days from the onset of differentiation should be allowed for stable expression of definitive neuronal markers to appear. A sufficient time is also required for a compound action on differentiation and/or proliferation to take place to a sufficient degree to be reliably detectable. Manifestation of drug-induced changes in neuron number takes a minimum of three days for the human cells to be detectable.

The final neuron number is detected by immunostaining of the culture with antibodies against neurons and quantified by counting of the immunopositive neurons and/or by measuring the staining intensity.

4. Method for Measuring Neurogenesis (1) Undifferentiated human neural stem/progenitor cells were harvested by enzyme treatment.

(2) The collected cells were seeded at 40,000 cells per well of 96-well plates pre-coated with extracellular matrix proteins (e.g., Biocoat PDL, Fisher). The seeding media is a standard serum-free, growth factor-free, basal media that supports healthy neuronal/glial survival, such as N2 without phenol red.

(3) Test agents at appropriate concentrations were added to each well on Day 0.

(4) The assay plates were incubated for 7 days, with 50% media change at every other day. On Day 2, 4, and 6 of post-plating, additional increment of the screening agents at appropriate concentrations were added to each well.

(5) On the final day of the culture (Day 7), alamar blue dye was added to each well and the cultures were further incubated for 2 hours at 37° C.

Figure 2:
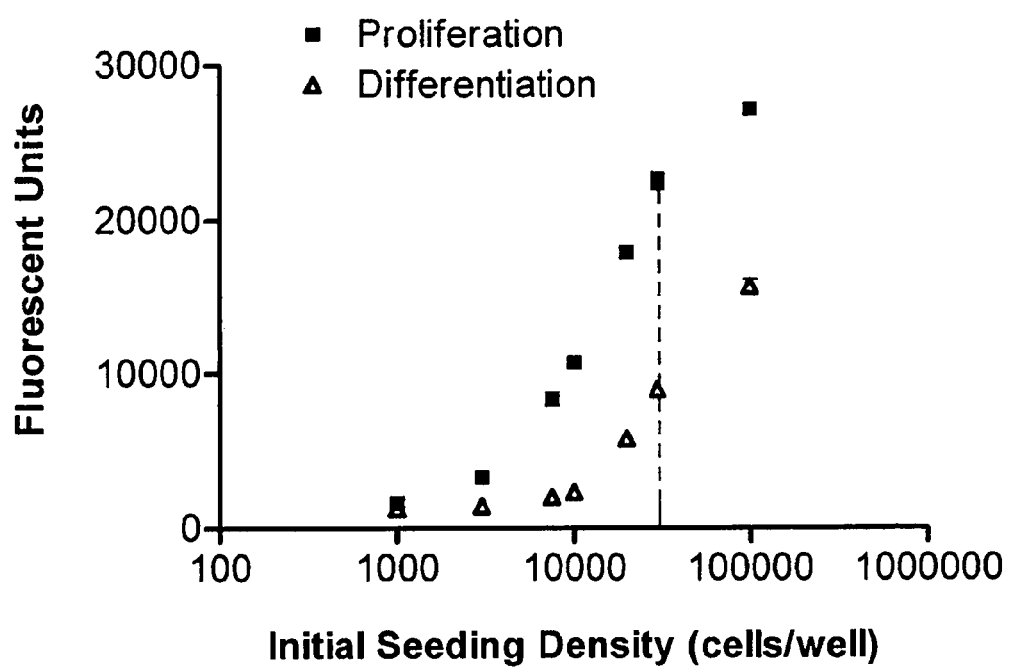
FIG. 2. Detection of changes in cell number by Alamar Blue dye. Alamar Blue, a fluorescent dye, is used as an indicator of metabolic respiration to determine optimum plating density. Results at an initial plating density of 30,000 cells/well suggest a large difference in cell number on removal of mitogen from the N2b media (differentiation) versus N2b with mitogen (proliferation) conditions. This figure only describes total cellular activity, further markers are required to determine what cell types (e.g. neuronal, glial) are observed under differentiating media.

(6) The fluorescence of the oxidized dye in each well was read by a fluorescent plate reader with the following settings:
Read Mode End Point
Excitation 530 nm, emission 590 nm, cutoff 570 nm The fluorescence level is proportional to the number of respiring cells in the culture and is a measure of a proliferative activity of a test agent (FIG. 2).

(7) After the alamar blue assay, the cells were fixed and stained with antibodies against neuron-specific antigens according to standard procedures. Typical antigens effective were Type III-beta tubulin and MAP2c.

(8) The total cell number in each well was quantified by staining the cultures with a nuclear dye such as DAPI or Hoechst according to standard procedures.

(9) As a preliminary detection of positive activities, the overall immunostaining intensity in each well was read by a fluorescence plate reader. For the positive hits, more quantitative analysis was carried out by automated morphometric counting of individual cells.

5. Examples

Example 1

Selection of a Positive Control

Figure 3A:
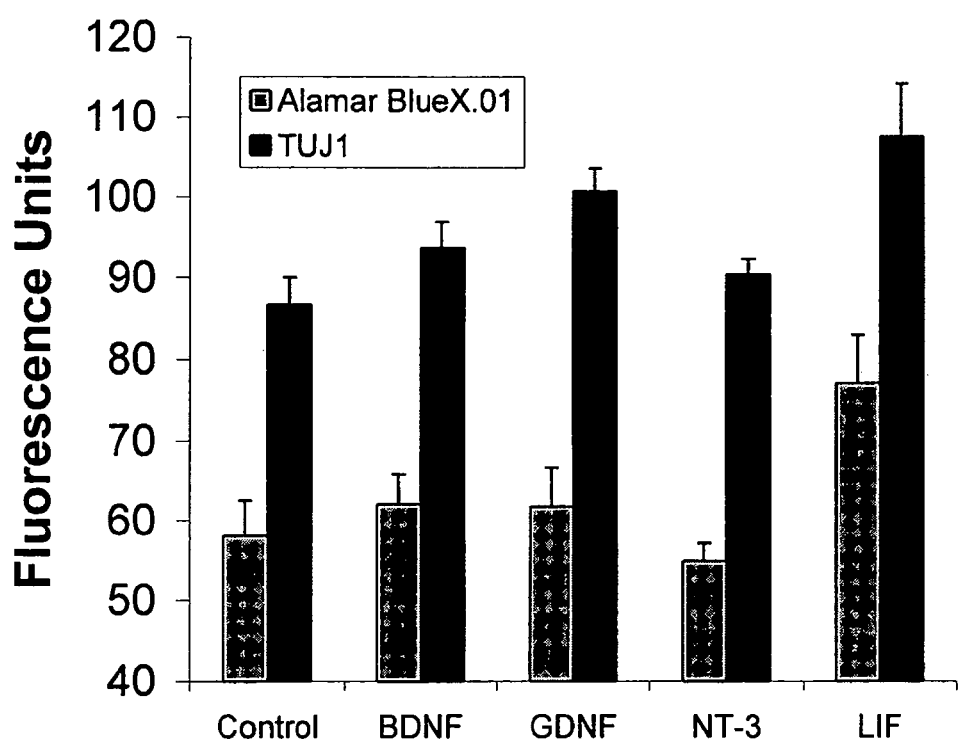
FIG. 3A. Influence of known growth factors on proliferation and neurogenesis relative to control. Hippocampal progenitor cells were treated for seven days with differentiation media (without mitogen) in the presence or absence of 20 ng/ml of growth factor dosed every other day. Plates were treated with Alamar Blue as described in Methods, then fixed and stained with antibody (TuJ1) against type III beta-tubulin (neuronal marker). The 96-well plate was read in a fluorescent plate reader. Bars represent the Mean+SD from 4 wells per treatment.
Figure 3B:
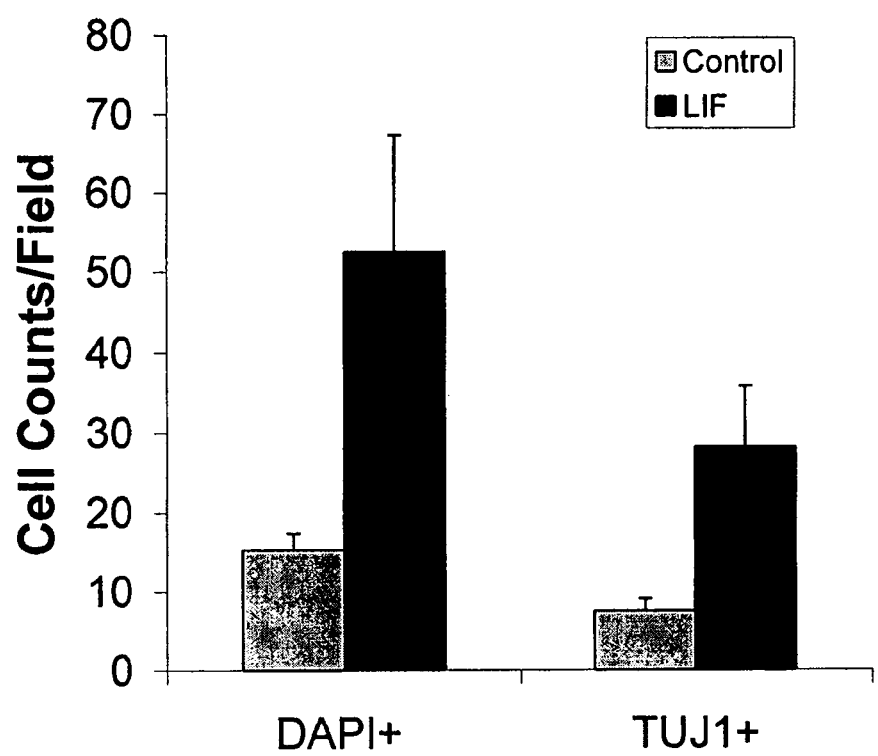
FIG. 3B. LIF effects on hippocampal cell proliferation and neurogenesis by manual cell counting. Hippocampal progenitor cells were treated for seven days with differentiation media (without mitogen) in the presence or absence of 20 ng/ml LIF. Three fields were analyzed per well for total number of cells (DAPI positive nuclei) and for total number of neurons (TUJI positive cells). Bars represent the Mean+SD from 4 wells per treatment. The percentage of neurons calculated for each treatment are as follows: 48.5+6.3% for controls and 53.6+1.15 for LIF. The non-TUJ1 positive cells are mainly astrocytic (GFAP+).

Several neurotrophic factors—including brain-derived neurotrophic factor, glia-derived neurotrophic factor, neurotrophic factor-3, and leukemia inhibitory factor—suggested to have neurogenic properties were tested in the assay described above. Only one (leukemia inhibitory factor) was effective (FIG. 3A and 3B). Thus, the assay can discriminate test agents for selectively having a neurogenic activity. The positive control utilized is leukemia inhibitory factor (LIF), a cytokine growth factor, at 20 ng/ml. The selection of LIF as the positive control is based on its properties to increase by 2-3 fold the number of neurons and glia. This effect validates both the neural stem cell system, in which, should a compound be effective in neurogenesis, the cells respond appropriately by enhanced differentiation and/or mitosis, and the assay method in which such cellular responses can be measured reproducibly and quantifiably.

Example 2

Figure 4:
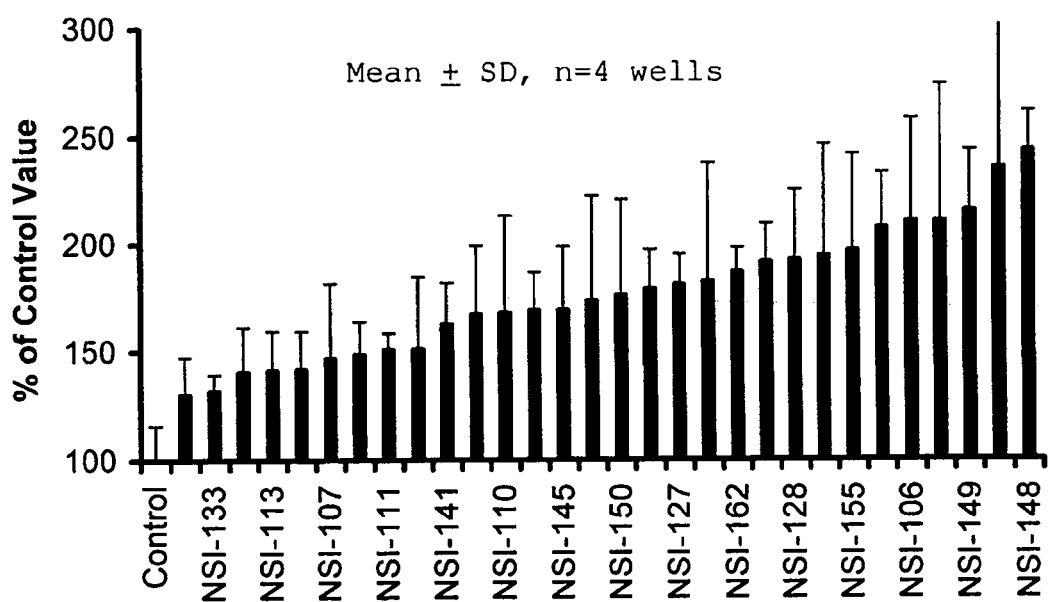
FIG. 4. Examples of proliferation profile of compounds selected from primary screening. Proliferation was measured after compound treatment for 7 days by Alamar Blue staining of live cells per well. Shown are relative values over the vehicle control.
Figure 5:
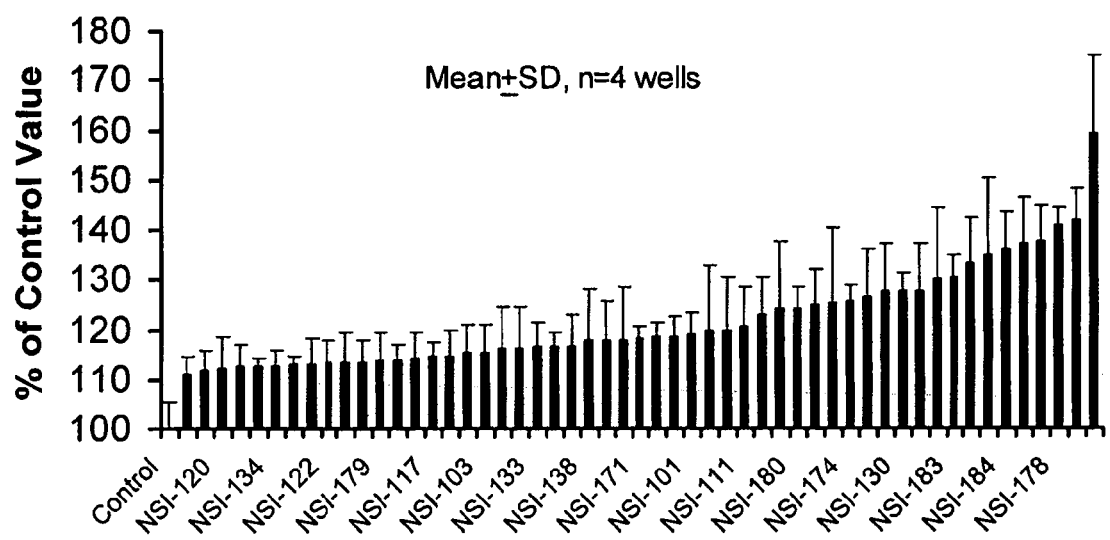
FIG. 5. Example of neurogenesis profile of compounds selected from primary screening. After 7 days of compound treatment, the ratio of neuron number (TuJ1 stained) to the total nuclei number (Hoechst stained) was determined. Shown are the relative ratio of neuron:total cells for each compound over the vehicle control in percentage. Typical ratio for vehicle control is 40-50% neurons. The ratio can change by either increased differentiation of the cells to neurons, decreased proliferation of astrocytes, or increased proliferation of neuronal progenitors.
Figure 6:
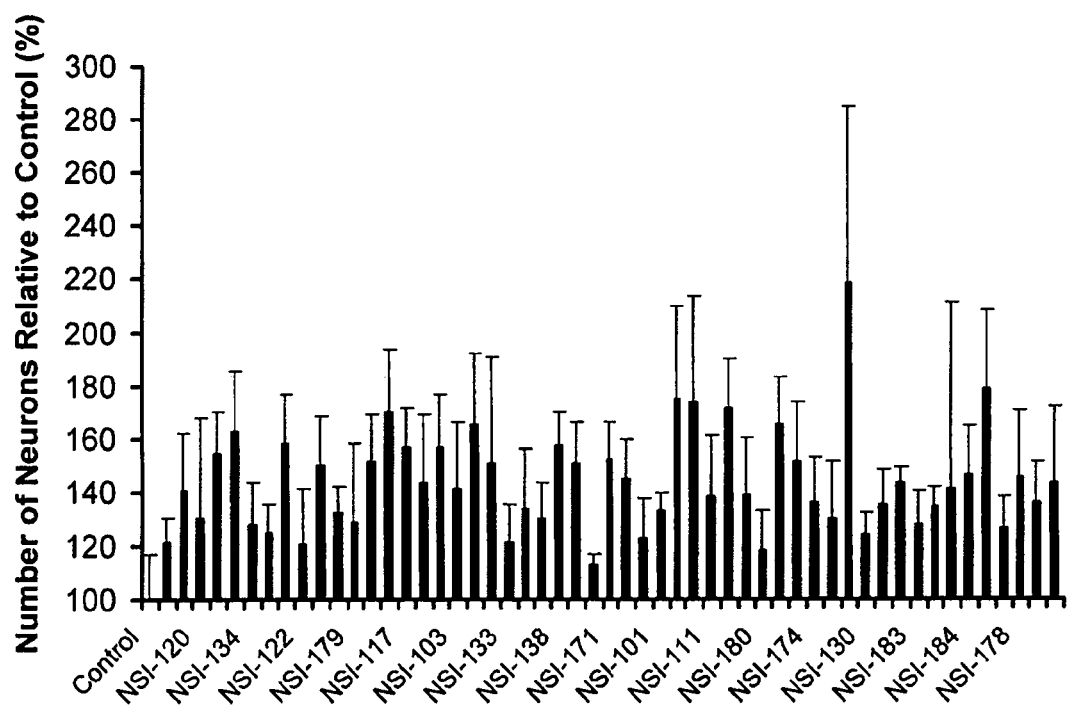
FIG. 6. Examples of neurogenesis profile of compounds selected from primary screening. After 7 days of compound treatment, the cells were stained with TuJ1 for neurons. The absolute number of TuJ1+ neurons per area was quantified and expressed as a relative value to the vehicle treated control.

Primary Screening of Unknown Compounds 5,628 synthetic compounds of the type Fused Imidazoles, Aminopyrimidines, Nicotinamides, Aminomethyl Phenoxypiperidines and Aryloxypiperidines are evaluated for their effect on neurogenesis according the assay method described above. From the preliminary analysis using the fluorescent plate reader, over 300 compounds to date showed initial positive activity. Those were re-analyzed by quantitative neuron counting. Among them, 30 compounds significantly increased cell number ("proliferation", FIG. 4); 53 increased the number of neurons ("neurogenesis", FIG. 5 & FIG. 6); and 7 showed significant activity in both. The significance level was empirically set at an activity above 30% change over the vehicle control for proliferation and above 10% change for neurogenesis. A summary of the result in the compound screening is provided in Table I.

TABLE I

Summary of Compound Screening

| Primary Screen | Hits Confirmed | Proliferation Hit | Neurogensis Hit | Double Hit |
|---|---|---|---|---|
| 0 | 0 | 0 | 0 | 0 |
| 2,240 | 88 | 13 | 8 | 1 |
| 5,628 | >300 | 30 | 53 | 7 |

Example 3

Dose-response Profiles

Figure 7:
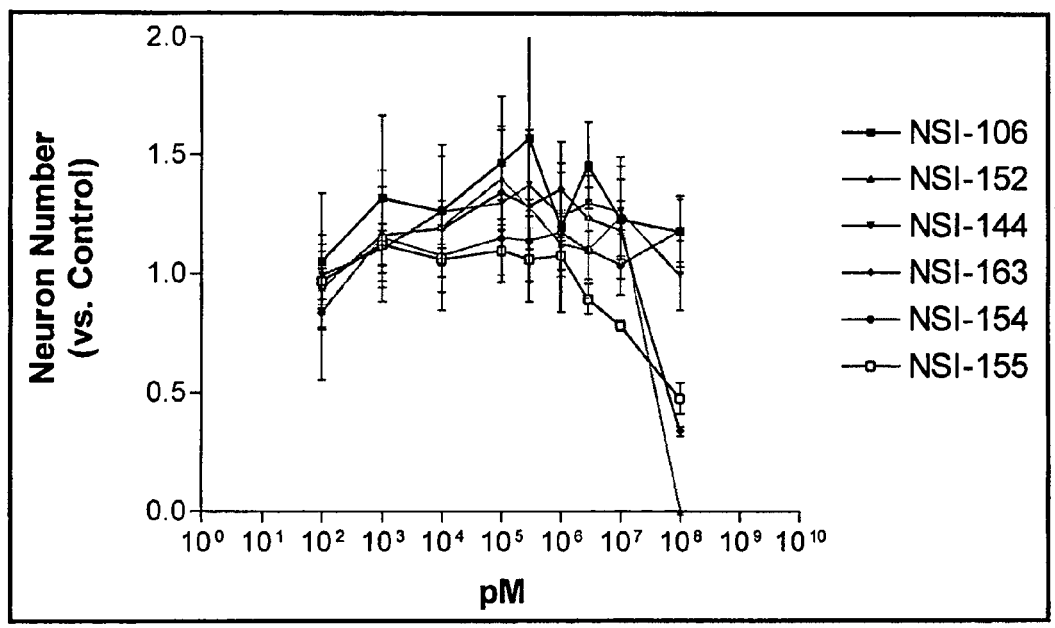
FIG. 7. Dose-dependent increase in neuron number. Differentiating human hippocampal progenitor cells were treated for 7 days with varying concentrations of "primary hits". Subsequently, the cells were fixed, stained with TuJ1, and positive cells were quantified by an automated cell counter. Shown are the number of neurons after each treatment normalized against the vehicle control (0 microM=1.0).

Linearity of dose-response and in vitro neurotoxicity are used to further filter down desired compounds from the primary screen. The dose-response curve measures neurogenesis over a concentration range of 100 picaM to 100 microM. The rationale for this is to eliminate early on those compounds with pronounced toxicity and those without a dose-dependent effect on neurogenesis. Examples of several primary hits fully analyzed for dose-response are shown in FIG. 7. Significantly, most compounds exhibit a linear response over several log concentrations below 1 microM. This indicates that the assay for primary screening is reliable and that the quality of the compound library is high. Table II contains the summary of EC50 of each compound tested. On the other hand, at high concentrations (100 microM), some, but not all showed high level of neurotoxicity, indicating that analyzing dose-response curves will be discriminatory and serve as an effective early filter.

TABLE II

Activity Profile of Primary Hits In Vitro

| Compound ID | Proliferation (% of Control) | Neuron Ratio (% of Control) | EC50 for Neuron Number | Other Characterization of Toxicity |
|---|---|---|---|---|
| NSI-106 | 211 ± 48 | 92 ± 6 | 0.1 nM $r^2$ 0.75 | No Toxicity |
| NSI-144 | 149 ± 15 | 137 ± 8 | 1.0 nM $r^2$ 0.54 | No Toxicity |
| NSI-152 | 174 ± 49 | 112 ± 4 | 0.1 nM $r^2$ 0.84 | Toxic At Highest Dose |
| NSI-154 | 211 ± 63 | 102 ± 6 | 0.3 nM $r^2$ 0.79 | No Toxicity |
| NSI-155 | 198 ± 44 | 118 ± 8 | 0.05 nM $r^2$ 0.49 | Toxic At Highest Dose |
| NSI-163 | 208 ± 25 | 120 ± 11 | 1.0 nM $r^2$ 0.81 | Toxic At Highest Dose |

Utilities of the Invention

In one aspect of this invention an agent would be administered to treat a neurodegenerative disease. In a preferred embodiment of this invention the neurodegenerative disease would be Alzheimer's disease, dementia, mild cognitive impairment, aged-related cognitive decline, Parkinson's disease, amyotrophic lateral sclerosis, multiple sclerosis, demyelination, stroke, spinal injuries, traumatic injuries, neuropathic pain, and the like.

In another aspect of this invention, the agent would be administered to treat a psychiatric disease. In a preferred embodiment of this invention the psychiatric disease is depression, post-traumatic stress syndrome, stress, anxiety, schizophrenia, sleep deprivation, cognitive dysfunction, amnesia, and the like.

In another aspect of the invention an agent would be administered by any number of routes and multipotent stem cells or differentiated multipotent stem cells would be transplanted into brain.

In another aspect of the invention the structures of the formula are utilized in above methods:

Structure Formula 1: fused imidazoles

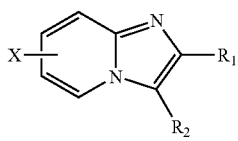

Structure Formula 2: aminopyrimidines.

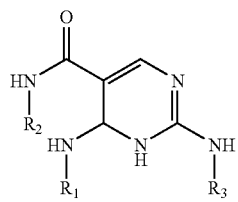

Structure Formula 3: nicotinamides

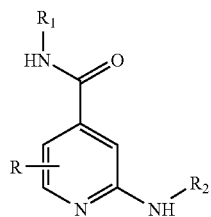

Structure Formula 4: aminomethyl phenoxypiperidines

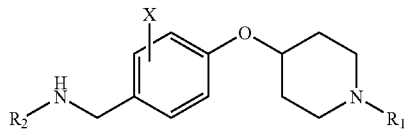

Structural Formula 5: aryloxypiperidines

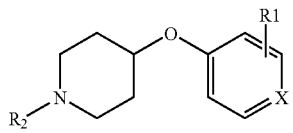

While the invention has been described in connection with what is presently considered to be the most practical and preferred embodiments, it is to be understood that the invention is not limited to the disclosed embodiments, but on the contrary is intended to cover various modifications and equivalent arrangements included within the spirit and scope of the appended claims.

Thus, it is to be understood that variations in the present invention can be made without departing from the novel aspects of this invention as defined in the claims.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of identifying a neurogenic agent, which comprises:
    (a) providing a stable human neural progenitor cell line, wherein
        (i) the cell line is derived from the hippocampus,
        (ii) the cell line has been expanded for at least ten cell doublings without substantially differentiating, and
        (iii) the cell line is capable of generating at least 40% neurons upon differentiation by mitogen withdrawal;
    (b) plating undifferentiated cells of said cell line into a culture with a serum-free, mitogen-free medium;
    (c) contacting the cells with a test agent which is a fused imidazole, an aminopyrimidine, a nicotinamide, an aminomethyl phenoxypiperidine or an aryloxypiperidine;
    (d) incubating the cells in the presence of the test agent for 3-7 days;
    (e) quantitatively determining the formation of neurons from said cells; and
    identifying the test agent as a neurogenic agent if said test agent increases the number or proportion of neurons by at least ten percent (10%).

2. The method of claim 1, wherein the cell line comprises a genetic modification to enhance the mitotic capacity of the cells.

3. The method of claim 2, wherein the genetic modification includes inducing overexpression of a c-myc protein fused to a ligand-binding domain of estrogen receptor.

* * * * *